US009069092B2

(12) United States Patent
Oreper et al.

(10) Patent No.: US 9,069,092 B2
(45) Date of Patent: Jun. 30, 2015

(54) X-RAY IMAGER WITH SPARSE DETECTOR ARRAY

(75) Inventors: Boris Oreper, Newton, MA (US); Andrew D. Foland, Wellesley, MA (US)

(73) Assignee: L-3 Communication Security and Detection Systems Corp., Woburn, MA (US)

( * ) Notice: Subject to any disclaimer, the term of this patent is extended or adjusted under 35 U.S.C. 154(b) by 602 days.

(21) Appl. No.: 13/413,601

(22) Filed: Mar. 6, 2012

(65) Prior Publication Data

US 2013/0235971 A1  Sep. 12, 2013

Related U.S. Application Data

(60) Provisional application No. 61/601,899, filed on Feb. 22, 2012.

(51) Int. Cl.
*G01N 23/04* (2006.01)
*G01V 5/00* (2006.01)
*B82Y 30/00* (2011.01)

(52) U.S. Cl.
CPC .......... *G01V 5/005* (2013.01); *G01N 2223/419* (2013.01); *G01N 2223/643* (2013.01); *B82Y 30/00* (2013.01)

(58) Field of Classification Search
CPC .................. G01N 2223/419; G01N 2223/643
USPC .................................................. 378/4–20, 57
See application file for complete search history.

(56) References Cited

U.S. PATENT DOCUMENTS

| 4,064,440 | A | 12/1977 | Roder |
| 4,131,798 | A | 12/1978 | Reddy et al. |
| 4,245,158 | A | 1/1981 | Burstein et al. |
| 4,366,382 | A | 12/1982 | Kotowski |
| 4,445,226 | A | 4/1984 | Brody |
| 4,686,695 | A | 8/1987 | Macovski |

(Continued)

FOREIGN PATENT DOCUMENTS

| DE | 197 56 697 A1 | 7/1999 |
| EP | 0 455 177 A2 | 11/1991 |

(Continued)

OTHER PUBLICATIONS

International Search Report and Written Opinion for International Application No. PCT/US04/012110 dated Feb. 8, 2005.

(Continued)

*Primary Examiner* — Hoon Song
(74) *Attorney, Agent, or Firm* — Wolf, Greenfield & Sacks, P.C.

(57) ABSTRACT

A system and method for imaging objects with a sparse detector array that includes fewer detectors than conventional x-ray scanning systems. The sparse detector array is positioned to receive x-ray radiation from the at least one x-ray source after passing through an inspection area. The sparse detector array includes a plurality of rows of detector elements, wherein at least some of the plurality of rows are separated by gaps such that the at least some of the plurality of rows are non-contiguous. An iterative reconstruction process is used to determine a volumetric image of the object from the radiation measurements recorded by the detectors in the sparse detector array.

31 Claims, 23 Drawing Sheets

(56) References Cited

U.S. PATENT DOCUMENTS

| | | |
|---|---|---|
| 4,823,371 A | 4/1989 | Grady |
| 4,942,596 A | 7/1990 | Eberhard et al. |
| 4,958,080 A | 9/1990 | Melcher |
| 5,040,199 A | 8/1991 | Stein |
| 5,044,002 A | 8/1991 | Stein |
| 5,247,561 A | 9/1993 | Kotowski |
| 5,442,672 A | 8/1995 | Bjorkholm et al. |
| 5,490,193 A | 2/1996 | Kuroda et al. |
| 5,490,196 A | 2/1996 | Rudich et al. |
| 5,642,393 A | 6/1997 | Krug et al. |
| 5,661,774 A | 8/1997 | Gordon et al. |
| 5,665,969 A | 9/1997 | Beusch |
| 5,796,802 A | 8/1998 | Gordon |
| 5,841,832 A | 11/1998 | Mazess et al. |
| 5,901,198 A | 5/1999 | Crawford et al. |
| 5,966,422 A | 10/1999 | Dafni et al. |
| 5,974,111 A | 10/1999 | Krug et al. |
| 6,018,562 A | 1/2000 | Willson |
| 6,067,342 A | 5/2000 | Gordon |
| 6,081,580 A | 6/2000 | Grodzins et al. |
| 6,118,125 A | 9/2000 | Carlson et al. |
| 6,188,747 B1 | 2/2001 | Geus et al. |
| 6,236,709 B1 | 5/2001 | Perry et al. |
| 6,248,990 B1 | 6/2001 | Pyyhtiä et al. |
| 6,421,420 B1 | 7/2002 | Grodzins et al. |
| 6,453,003 B1 | 9/2002 | Springer et al. |
| 6,459,755 B1 | 10/2002 | Li |
| 6,473,487 B1 | 10/2002 | Le |
| 6,535,626 B1 | 3/2003 | Pressman et al. |
| 6,570,958 B2 | 5/2003 | Brendler |
| 6,597,760 B2 | 7/2003 | Beneke et al. |
| 6,628,745 B1 | 9/2003 | Annis et al. |
| 6,862,335 B2 | 3/2005 | Basu et al. |
| 6,944,268 B2 | 9/2005 | Shimono |
| 7,016,459 B2 | 3/2006 | Ellenbogen et al. |
| 7,020,241 B2 | 3/2006 | Beneke et al. |
| 7,120,222 B2 | 10/2006 | Hoffman |
| 7,120,283 B2 | 10/2006 | Thieret et al. |
| 7,203,276 B2 | 4/2007 | Arsenault et al. |
| 7,233,644 B1 | 6/2007 | Bendahan et al. |
| 7,319,737 B2 | 1/2008 | Singh |
| 7,369,642 B2 | 5/2008 | Eilbert et al. |
| 7,428,292 B2 * | 9/2008 | De Man et al. ............... 378/9 |
| 7,431,500 B2 | 10/2008 | Deych et al. |
| 7,529,344 B2 | 5/2009 | Oreper |
| 7,606,348 B2 | 10/2009 | Foland et al. |
| 7,606,349 B2 | 10/2009 | Oreper et al. |
| 7,616,729 B2 | 11/2009 | Vengrinovich et al. |
| 7,660,391 B2 | 2/2010 | Oreper et al. |
| 7,672,427 B2 | 3/2010 | Chen et al. |
| 7,809,104 B2 | 10/2010 | Foland |
| 7,831,012 B2 | 11/2010 | Foland et al. |
| 7,885,372 B2 | 2/2011 | Edic et al. |
| 8,270,565 B2 | 9/2012 | Oreper |
| 8,423,125 B2 | 4/2013 | Rousso et al. |
| 8,644,549 B2 | 2/2014 | Foland et al. |
| 2002/0094059 A1 | 7/2002 | Grodzins |
| 2003/0190011 A1 | 10/2003 | Beneke et al. |
| 2004/0086074 A1 | 5/2004 | Taguchi |
| 2005/0111610 A1 | 5/2005 | De Man et al. |
| 2005/0135550 A1 | 6/2005 | Man et al. |
| 2006/0023835 A1 | 2/2006 | Seppi |
| 2006/0062443 A1 | 3/2006 | Basu et al. |
| 2006/0104410 A1 † | 5/2006 | Sauer et al. |
| 2006/0233302 A1 | 10/2006 | Might et al. |
| 2007/0009088 A1 † | 1/2007 | Edic et al. |
| 2007/0025505 A1 | 2/2007 | Bjorkholm |
| 2007/0133744 A1 | 6/2007 | Bijjani |
| 2007/0205367 A1 * | 9/2007 | Deman et al. ............ 250/363.02 |
| 2008/0025461 A1 | 1/2008 | Foland et al. |
| 2008/0043917 A1 | 2/2008 | Oreper |
| 2008/0095317 A1 | 4/2008 | Lemaitre |
| 2008/0170655 A1 | 7/2008 | Bandahan |
| 2008/0267480 A1 | 10/2008 | Nielsen et al. |
| 2008/0273651 A1 | 11/2008 | Boas |
| 2010/0020922 A1 * | 1/2010 | Carmi ............................ 378/19 |
| 2010/0215142 A1 * | 8/2010 | Dafni et al. .................... 378/19 |
| 2010/0278296 A1 | 11/2010 | Edic et al. |
| 2010/0316188 A1 | 12/2010 | Eilbert |
| 2011/0064190 A1 | 3/2011 | Ruimi et al. |
| 2011/0116600 A1 | 5/2011 | Morton |
| 2011/0280367 A1 * | 11/2011 | Baeumer et al. ................. 378/9 |
| 2011/0293158 A1 | 12/2011 | Popescu |
| 2012/0093280 A1 | 4/2012 | Konno et al. |
| 2012/0134531 A1 † | 5/2012 | Zhang et al. |
| 2012/0195458 A1 | 8/2012 | Foland et al. |
| 2013/0016805 A1 | 1/2013 | Silver |
| 2014/0037045 A1 * | 2/2014 | Dafni et al. ..................... 378/5 |

FOREIGN PATENT DOCUMENTS

| | | |
|---|---|---|
| JP | 2000-111501 A | 4/2000 |
| JP | 2002-168802 A | 6/2002 |
| WO | WO 92/03837 A1 | 3/1992 |
| WO | 9901736 A2 † | 1/1999 |
| WO | WO 2004/010127 A1 | 1/2004 |
| WO | WO 2004/095060 A2 | 11/2004 |
| WO | WO 2004/095060 A3 | 4/2005 |
| WO | WO 2006129282 A1 | 12/2006 |
| WO | WO 2008027703 A2 | 3/2008 |
| WO | WO 2012/003850 A1 | 1/2012 |
| WO | WO 2012112153 A1 | 8/2012 |

OTHER PUBLICATIONS

International Search Report for International Application No. PCT/US2006/044195 dated Mar. 18, 2008, 5 pages.
Invitation to Pay Additional Fees for International Application No. PCT/US2007/003606 dated Mar. 11, 2008.
International Search Report and Written Opinion for International Application No. PCT/US2007/003606 dated May 20, 2008.
International Preliminary Report on Patentability for International Application No. PCT/US2007/003606 dated Aug. 12, 2008.
International Search Report and Written Opinion for International Application No. PCT/US2007/020542 dated Jul. 17, 2008.
International Search Report and Written Opinion for International Application No. PCT/US2010/001353 dated Dec. 17, 2010.
International Preliminary Report on Patentability for International Application No. PCT/US2010/001353 dated Nov. 17, 2011.
Invitation to Pay Additional Fees for International Application No. PCT/US2012/023529 mailed May 3, 2012.
Written Opinion for International Application No. PCT/US2012/023529 mailed May 6, 2013.
International Preliminary Report on Patentability for International Application No. PCT/US2012/023529 mailed Nov. 7, 2013.
Invitation to Pay Additional Fees for PCT/US2014/011054 mailed May 8, 2014.
Invitation to Pay Additional Fees for International Application No. PCT/US2013/027256 dated Aug. 2, 2013.
Invitation to Pay Additional Fees for International Application No. PCT/US2013/027256 dated Jan. 27, 2014.
Written Opinion for International Application No. PCT/US2013/027256 dated Mar. 17, 2014.
[No Author Listed] "Nuclear Instruments and Methds in Physics Research Section A: Accelerators, Spectrometers, Detectors Table of Contents of and Associated Equipment," vol. 491, Issues 1-2, pp. 1-350 (Sep. 21, 2002), from Science Direct website http://www.sciencedirect.com/science, pp. 1-5, printed out Mar. 5, 2004.
[No Author Listed] Rapiscan MVXR 500, Hold Baggage Screening System, printed from www.rapiscansystems.com, pp. 4.
[No Author Listed] Smiths Heimann, Hi-Scan 10080 EDtS X-ray Inspection Systems, Jan. 13, 2003, pp. 2.
Baron "A Refractive Collimator for Synchrotron Radiation" Spring-8 Instrumentation & Techniques; 1999; pp. 51-52.
Caria, Mario, Ed., "Radiation Imaging Detectors," Proceedings of the 3$^{rd}$ International Workshop on Radiation Imaging Detectors, Orosei, Sardinia, Italy, Sep. 23-27, 2001, Table of Contents.
De Man, B. et al., "A Study of Four Minimization Approaches for Iterative Reconstruction in X-ray CT", 2005 IEEE Nuclear Science

(56) References Cited

OTHER PUBLICATIONS

Symposium Conference Record, Wyndham El Conquistator Resort, Puerto Rico, Oct. 23-29, 2005, vol. 5, pp. 2708-2710.
Fischer, P., et al., "Single Photon Counting X-ray Imaging with Si and CdTe Single Chip Pixel Detectors and Multichip Pixel Modules," 3$^{rd}$ Int'l Workshop on Radiation Imaging Detectors, Orosei, Sardinia, Sep. 24-27, 2001.
Forth "Design and Fabrication of Compound Refractive X-ray Lenses for CHESS" Dept. of Physics, Oberlin College, Ohio; 2000; pp. 1-9.
Goitein, "Three dimensional density reconstruction from a series of two-dimensional projections," Nuclear Instruments and Methods, vol. 101(1972), 509-518.
Graeme, Jerald G., "Photodiode Amplifiers: Op Amp Solutions," McGraw-Hill, 1995, pp. v-31.
Kawata, S. et al., "Constrained Iterative Reconstruction by the Conjugate Gradient Method", IEEE Trans. on Med. Imaging, vol. MI-4, No. 2, Jun. 1, 1985, pp. 65-71.
Kuyumchyan et al. "Study of optical properties of x-ray system based on two zone plates" IMT RAS Chernogolovka, Moskow District, Russia; Jul. 2005; 5 pages.
Melcher, C.L., et al., "A promising new scintillator: cerium-doped lutetium oxyorthosilicate," Nuclear Instruments and Methods in Physics Research, A314 (1992) pp. 212-214.
Pereira et al. "Large Aperture X-ray refractive Lens from Lithium" Dept. of Physics, University of Michigan; Nov. 2004; pp. 174-184; vol. 5539.
Pereira et al. "Lithium X-ray Refractive Lenses" Dept. of Physics, University of Michigan, Dec. 2002; 2 pages.
Pereira et al. "Parabolic lithium refractive optics for x-rays" Review of Scientific Instruments, Jan. 2004, pp. 37-41; vol. 75.
Roder, F.L., "Explosives Detection by Dual-Energy Computed Tomography (CT)", SPIE, vol. 192, pp. 171-178, 1979.
Roder, F.L., "Principles, History, and Status of Dual-Energy Computerized Tomographic Explosives Detection," Journal of Testing and Evaluations, vol. 13, No. 3, May 1985, pp. 211-216.
Roder, F.L., "The Evolution of Computed Tomography (CT) as an Explosives Detection Modality," Proc. 1 International Symposium on Explosive Detection Technology, 1991, pp. 297-308.
Schirato, R.C., et al., "Development of monolithic $Cd_{1-x}Zn_x Te$ arrays with improved energy and spatial resolution," SPIE, vol. 2278 X-Ray and UV Detectors (1994), pp. 47-56.
Turchetta, R., et al., "High Spatial Resolution Silicon Read-Out System for Single Photon X-Ray Detection," IEEE Trans. Nuclear Science 41(4):1063-1068 (1994).
Van Eijk, C.W.E., "New inorganic scintillators—aspects of energy resolution," Nuclear Instruments and Methods in Physics Research, A471 (2001) pp. 244-248.
Zbijewski, W. et al., "Suppression of Intensity Transition Artifacts in Statistical X-ray Computer Tomography Reconstruction through Radon Inversion Initialization", Med. Phys., AIP, Melville, NY, vol. 31, No. 1, Jan. 1, 2004, pp. 62-69.
Q. Xue et al., "A local reconstruction method for low-energy gamma-ray computed tomography system", IOPscience, 14 pps., 2011.
Pinhas Ephrat et al., "Four-dimensional photoacoustic imaging of moving targets", Optics Express, pp. 21570-21581, Dec. 22, 2008.
Yinsheng Li et al., "Strategy of computed tomography sinogram inpainting based on sinusoid-like curve decomposition and eigenvector-guided interpolation", Optical Society of America, vol. 29, No. 1, pp. 153-163, Jan. 2012.
Cao, et al., "A dynamic micro-CT scanner based on a carbon nanotube-based dynamic micro-CT scanner," Physics in Medicine and Biology, Institute of Physics Publishing, Bristol GB, vol. 54, No. 8, Apr. 21, 2009.
Mehranian, et al., "Sparsity constrained sonogram inpainting for metal artifact reduction in x-ray compouted tomography," Nuclear Sciense Symposium and Medical Imaging Conference (NSS/MIC), Oct. 23, 2011.
Zbijewski, et al., "Statistical reconstruction for x-ray CT systems with non-continuous detectors," Physics in Medicine and Biology, Institute of Physics Publishing, Bristol GB, vol. 52, No. 2, Jan. 21, 2007.
International Search Report for PCT/US2013/027256 dated Sep. 25, 2013.
Lemmens et al., Suppression of Metal Artifacts in CT Using a Reconstruction Procedure that Combines MAP and Projection Completion, IEEE Transactions on Medical Imaging, vol. 28, No. 2, pp. 250-260, Feb. 2009.†

\* cited by examiner
† cited by third party

X-RAY IMAGER WITH SPARSE DETECTOR ARRAY

This application claims priority under 35 U.S.C. §119(e) to U.S. Provisional Application Ser. No. 61/601,899 filed Feb. 22, 2012 and entitled "Volumetric X-Ray Imager With Sparse Detector Coverage," the entire contents of which is incorporated herein by reference.

BACKGROUND

X-ray imaging technology has been employed in a wide range of applications from medical imaging to detection of unauthorized objects or materials in baggage, cargo or other containers generally opaque to the human eye. X-ray imaging typically includes passing high-energy radiation (i.e., X-rays) through an object to be imaged. X-rays from a source passing through the object interact with the internal structures of the object and are altered according to various characteristics of the material (e.g., transmission, scattering and diffraction characteristics, etc.). By measuring changes (e.g., attenuation) in the X-ray radiation that exits the object, information related to material through which the radiation passed may be obtained to form an image of the object.

In order to measure X-ray radiation penetrating an object to be imaged, an array of detectors responsive to X-ray radiation typically is arranged on one side of the object opposite a radiation source. The magnitude of the radiation, measured by any detector in the array, represents the density of material along a ray from the X-ray source to the X-ray detector. Measurements for multiple such rays passing through generally parallel planes through the object can be grouped into a projection image. Each such measurement represents a data point, or "pixel," in the projection image.

Projection imaging is well suited for finding objects that have material properties or other characteristics such that they produce a group of pixels having a recognizable outline regardless of the orientation of the object to be imaged. However, projection images are not well suited for reliably detecting or characterizing objects that have at least one relatively thin dimension, particularly if these objects may be packaged with other objects, as often occurs in security inspection scenarios. If the rays of radiation pass through only a thin portion of the object or pass through multiple objects, there may be no group of pixels in the projection image that has characteristics significantly different from other pixels in the image. The object may not be well characterized by, or even be detected in, the resultant projection image.

Measuring attenuation of X-rays passing through an object from multiple different directions can provide more accurate detection of relatively thin objects. For instance, in a CT scanner, such measurements may be obtained by placing the X-ray source and detectors on a rotating gantry. An object to be imaged passes through an opening in the center of the gantry. As the gantry rotates around the object, measurements are made on rays of radiation passing through the object from many different directions.

Multiple projection images can be used to construct a three-dimensional, or volumetric, image of the object. A volumetric image is organized in three-dimensional sub-blocks called "voxels"—analogous to pixels in a two-dimensional image—with each voxel corresponding to a density (or other material property) value of the object at a location in three-dimensional space. Even relatively thin objects may form a recognizable group of voxels in such a volumetric image.

The process of using multiple radiation measurements from different angles through an object to compute a volumetric image of the object is herein referred to as volumetric image reconstruction. The quality of volumetric image reconstruction not only depends on the geometry of the imaged object, but also on the geometry of the imaging system including the relative positions of X-ray sources and detectors used to make the measurements. The relative positions of sources and detectors control the set of angles from which each voxel is irradiated by X-rays.

Conventional approaches to volumetric image reconstruction fall into one of two classes: direct reconstruction methods based on formal mathematical solutions to the problem, and iterative reconstruction methods, which calculate the final image in a sequence of small steps. Examples of direct reconstruction methods include filtered back projection and Fourier reconstruction, while examples of iterative reconstruction methods include the Algebraic Reconstruction Technique (ART) and the Simultaneous Iterative Reconstruction Technique (SIRT).

SUMMARY

The inventors have recognized and appreciated that inspection systems may be manufactured in a cost effective manner, but still produce accurate images, by using a sparse detector array having fewer detectors than a full detector array. The reduced number of radiation measurements in such a system resulting from the use of fewer detectors may be compensated, at least in part, by reconstructing volumetric images using iterative reconstruction methods.

In one aspect, the invention relates to an inspection apparatus comprising an inspection area; at least one x-ray source adapted to emit x-ray radiation into the inspection area; and a sparse detector array positioned to receive x-ray radiation from the at least one x-ray source after passing through the inspection area, wherein the sparse detector array includes a plurality of rows of detector elements, wherein at least some of the plurality of rows are separated by gaps such that the at least some of the plurality of rows are non-contiguous.

In another aspect, the invention relates to a computer-implemented method for deriving a volumetric image of an object in an inspection area of an x-ray system, wherein the x-ray system includes a sparse detector array having a plurality of non-contiguous rows of detector elements. The method comprises receiving at the detector elements in the sparse detector array, a plurality of radiation measurements indicating amounts of radiation passing through the object from different directions, wherein the plurality of radiation measurements include sparsely-spaced measurements in a fan-beam direction of radiation passing through the object; and performing at least one iteration of an iterative reconstruction process from the plurality of radiation measurements to derive the volumetric image of the object.

In another aspect, the invention relates to an inspection system, comprising: at least one x-ray source positioned to emit x-ray radiation toward an inspection area in a tunnel, wherein the tunnel includes a conveyor configured to enable an object placed thereon to pass through the inspection area; and a sparse detector array positioned to receive the x-ray radiation passing through the object, wherein the sparse detector array includes a plurality of rows of detector elements, wherein the detector elements in each row are oriented along the moving direction of the conveyor, and wherein the sparse detector array includes gaps between at least some of the plurality of rows in a direction perpendicular to the moving direction of the conveyor.

DETAILED DESCRIPTION

Embodiments of the present disclosure may be used to form a volumetric image of an object imaged by an imaging system. The methods for constructing volumetric images described hereinafter may be applied to any of numerous imaging systems including medical imaging systems, animal imaging systems, non-destructive testing systems, and inspection systems used to image, for example, cargo and luggage. One such inspection system is illustrated in FIG. 1.

Figure 1:
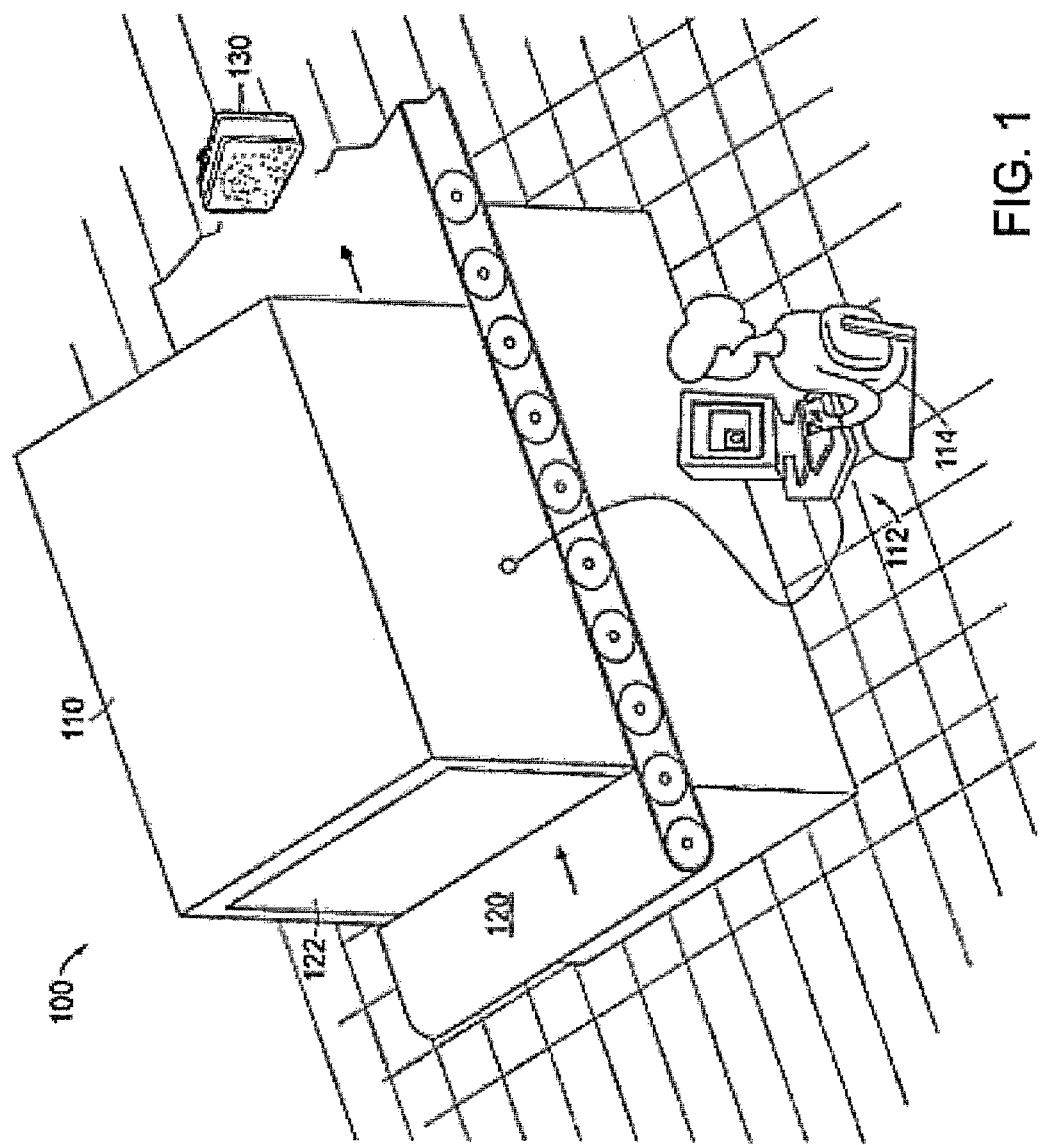
FIG. 1 is a sketch of a security checkpoint employing an imaging inspection system, in accordance with some embodiments of the present disclosure.

FIG. 1 illustrates a security checkpoint 100 at which an illustrative imaging system for inspecting objects may be employed. Checkpoint 100 may be a checkpoint used at any facility at which it is desired to create a secured area. For example, at an airport, checkpoint 100 may be located at the entrance to boarding gates. In such an embodiment, passenger carry on luggage may be inspected at checkpoint 100. Alternatively, checkpoint 100 may be positioned at an airport to inspect checked baggage before it is loaded on airplanes. However, an inspection system according to embodiments of the invention is not limited for use at airports, and checkpoint 100 may be a checkpoint located in any suitable setting. For example, checkpoint 100 may be located at a border crossing.

Checkpoint 100 includes inspection system 110. As described in greater detail below, inspection system 110 produces volumetric images of items under inspection. In the example of FIG. 1, item under inspection 130 is pictured as a suitcase. However, inspection system 110 may operate on any suitable type of item under inspection, such as other forms of luggage, carry-on items, parcels, or any other container in which contraband objects, or any other objects of interest, may be concealed.

In the embodiment shown, inspection system 110 includes a conveyor 120. Items under inspection 130 are placed on conveyor 120 and moved through tunnel 122. Within tunnel 122, one or more x-ray sources are positioned to direct radiation at items on conveyor 120. One or more detector arrays are positioned to receive radiation from the x-ray source(s) after the radiation has passed through an item under inspection.

Measurements of the detector outputs can be used to form a volumetric image of the item under inspection. Outputs of the detectors may be passed to computer 112. Computer 112 processes the outputs of the detectors to form a volumetric image of each item under inspection. Each volumetric image may be analyzed to detect suspicious regions within the image.

The volumetric image may be formed from radiation measurements from multiple directions of the item under inspection. Volumetric image reconstruction methods may be applied to the plurality of measurements obtained by the detectors to form the volumetric image.

Any of suitable iterative volumetric image reconstruction methods may be applied to form the volumetric image of an item under inspection from multiple radiation measurements from different angles of the item, including techniques as are known in the art. For example, iterative reconstruction approaches such as the algebraic reconstruction technique (ART), iterative re-weighted least squares, and expectation maximization may be applied.

The volumetric image may depict a characteristic of an item under inspection. For example, the magnitude of the radiation received may be compared to the magnitude of the radiation emitted by the x-ray sources to determine attenuation of the radiation within the item under inspection. Attenuation is a function of density of the item. Accordingly, forming the image using attenuation measurements may result in a volumetric image depicting the density of objects within the item under inspection.

Other material properties may alternatively or additionally be depicted in a volumetric image. For example, the ratio of attenuation of radiation at different energy levels can indicate atomic number of material through which the radiation passes. Accordingly, if the at least one source emits radiation of at least two energies and the detectors can be operated to measure attenuation of radiation of these different energies. A ratio of attenuations may be depicted in the image, in which case the volumetric image may represent the atomic number of objects within the item under inspection.

In some embodiments, measurements may be represented using basis function decomposition. The sum of the weighted basis functions may represent the spatial function of object properties, for instance either density, or effective atomic number. In such an embodiment, the values in the volumetric image may represent weighting of basis functions computed during the decomposition.

In yet further embodiments, an image may represent a combination of characteristics. For example, both density and atomic number could be represented in an image. Thus, the specific characteristic measured and the interpretation of that characteristic is not a limitation on the invention.

Image analysis may be performed by displaying a visual representation of the image for a human operator 114. Additionally, computer processing within computer 112 may process the volumetric images using automatic detection algorithms to identify suspicious regions. In the embodiment illustrated in FIG. 1, once suspicious regions are identified by computer processing, those regions are highlighted in a visual image displayed for human operator 114. However, in other embodiments, image processing may be performed solely by a human operator 114. In yet other embodiments, image processing may be performed solely by a computer. Accordingly, the nature of image processing performed is not a limitation on the invention and any suitable type of image processing may be performed.

In the embodiment illustrated, computer 112 is shown as a desktop computer workstation located at checkpoint 100. However, the type and location of computer 112 is not a limitation on the invention. For example, computer 112 may be integrated into the chassis of inspection system 110. Alternatively, computer 112 may be connected to inspection system 110 over a network link. If computer 112 is connected over a network link, computer 112 may be located at any suitable location reachable by the network and does not need to be physically located at checkpoint 100. Further, computer 112 is shown as a single computer. However, a collection of one or more computers may be used to process data collected by inspection system 110. If processing is performed in multiple computers, it is not necessary that the computers be located together. Accordingly, computer 112 should be understood to represent one or more computer processors located in any suitable location or locations that may perform processing on the data collected by inspection system 110.

Figure 2:
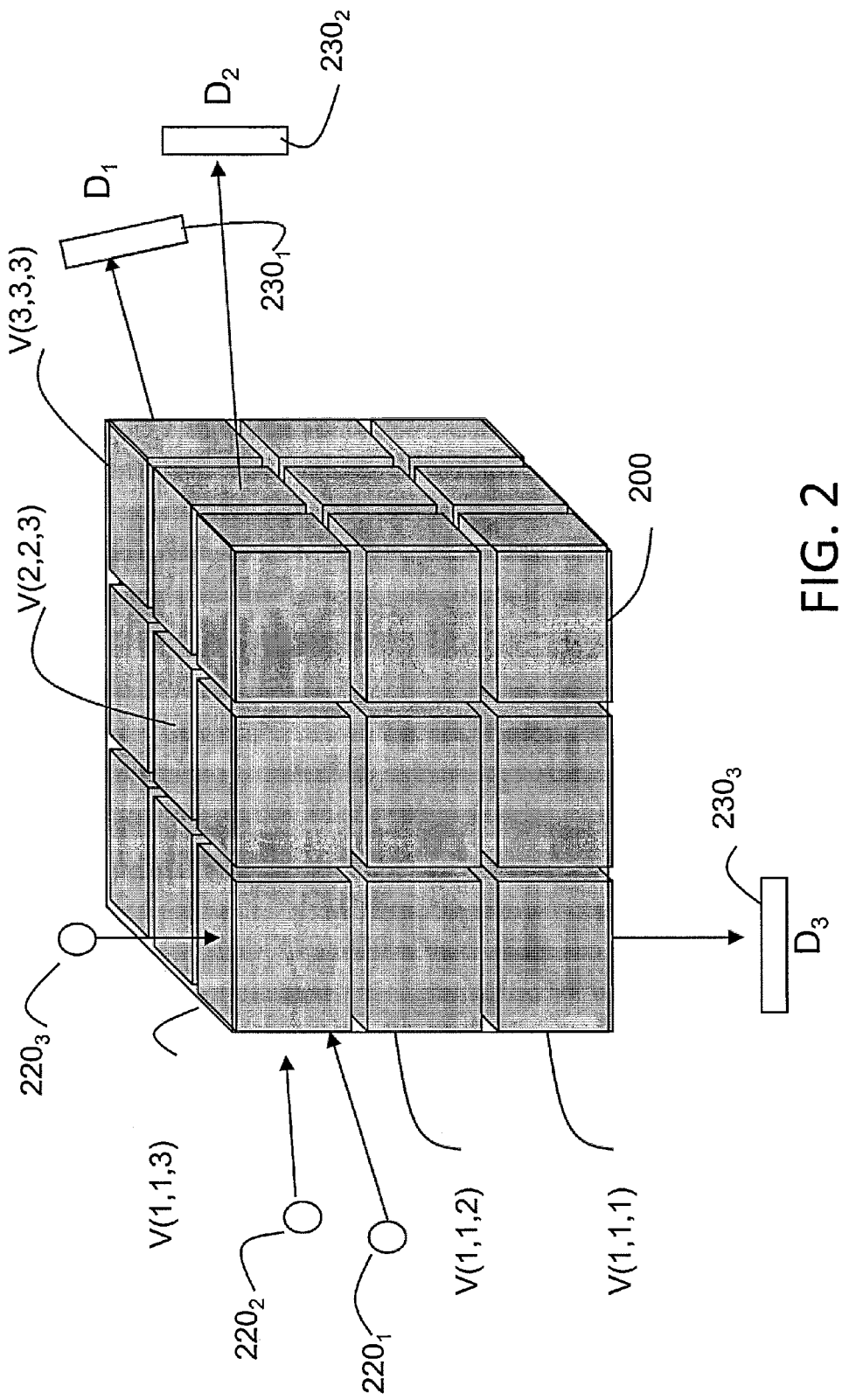
FIG. 2 is a sketch illustrating aspects of forming a multiview volumetric image, in accordance with some embodiments of the present disclosure.

FIG. 2 is a sketch demonstrating aspects of computing a volumetric image from measurements made on an item under inspection 200. In the simple example of FIG. 2, the item under inspection 200 is divided into nine regions. An image of item under inspection 200 is formed by computing a property of the material in each of these nine regions. Each of the nine regions will correspond to a voxel in the computed image. For this reason the regions in the item under inspection are sometimes also referred to as "voxels." In the simple example of FIG. 2, item under inspection 200 is divided into nine voxels of which V(1,1,1), V(1,1,2), V(1,1,3), V(2,2,3) and V(3,3,3) are numbered. To form a volumetric image of item under inspection 200, a material property is computed for each of the voxels from the measured outputs of detectors, of which detectors $230_1$, $230_2$ and $230_3$ are shown. In the illustrated embodiment, the material property is an average density of the material within the voxel.

In the embodiment illustrated, measurements from which density may be computed are made by passing rays of radiation through item under inspection 200 from different directions. By measuring the intensity of the rays after they have passed through the item under inspection and comparing the measured intensity to incident intensity, attenuation along the path of the ray may be determined. If attenuation along a sufficient number of rays traveling in a sufficient number of directions is measured, the data collected can be processed to compute the density within each of the voxels individually.

For example, FIG. 2 shows a source $220_1$ and a detector $230_1$. A ray traveling from source $220_1$ to detector $230_1$ passes through voxels V(1,1,3), V(2,2,3) and V(3,3,3). As a result, the value measured at detector $230_1$ will depend on the densities in each of those voxels. Thus, the measurement taken at detector $230_1$ of a ray from source $220_1$ may be used to estimate the density at each of the voxels V(1,1,3), V(2,2,3) and V(3,3,3).

As shown, a ray from source $220_1$ to detector $230_1$ represents just one of the rays passing through item under inspection 200. Other rays are shown in the example of FIG. 2. For example, a ray is shown passing from source $220_2$ to detector $230_2$. As with the ray passing from source $220_1$ to detector $230_1$, the value measured at detector $230_2$ will depend on the densities of voxels V(1,1,3), V(2,2,3) and V(3,2,3) because the ray source $220_2$ passes through these voxels before impinging on detector $230_2$. Similarly, the value measured at detector $230_3$, with respect to a ray passing from passing from source $220_3$ to detector $230_3$, is influenced by the densities of the voxels along that ray (V(1,1,1), V(1,1,2), and V(1,1,3)).

FIG. 2 shows only three rays passing through item under inspection 200. Each of the rays generates a single measurement representative of the densities of voxels, through which the ray passes, in item under inspection 200. In the simple problem illustrated in FIG. 2, item under inspection 200 is divided into 27 voxels. Accordingly, though FIG. 2 shows only three rays passing through item under inspection 200, to compute a volumetric image of item under inspection 200, more measurements are typically needed.

In a physical system, the number of measurements taken often exceeds the number of voxels in the image. For instance, measurements may be made such that multiple rays pass through each voxel with some of the rays passing through each voxel from a range of angles. The range of angles may be any suitable range. For example, it may be desirable to have rays passing through the item under inspection from a range of angles that exceeds 180°, or a range of angles that is as close to 180° as possible. Though in other scenarios the range of angles may be smaller, for instance a range such less than 140°, 150°, 160°, or 170° may be used.

Measurements obtained from multiple rays passing through the object under inspection may be used to compute a volumetric image. For instance, if a sufficient number of measurements along rays from a sufficient number of independent angles are made, the measured outputs of the detectors may be used to define a system of simultaneous equations that, using an iterative mathematical technique, may be solved for the unknown values representing the densities of the individual voxels in item under inspection 200.

Uncertainty or other variations in the measurement process may prevent a single solution from satisfying simultaneously all equations in a system of equations formed from the measurements. Thus, solving the system of equations formed from actual measurements would involve finding the values that best solve the equations. Similarly, obtaining measurements from multiple angles will allow voxels to be computed using a direct method.

An example of an iterative method, termed the algebraic reconstruction technique (ART) computes a value $\rho$ for each of the voxels in the item under inspection. A maximum likelihood estimate $M^2$ is defined as:

$$M^2(\hat{\rho}_k) = \sum_i \frac{(X_i(\hat{\rho}_k) - x_i)^2}{\sigma_i^2},$$

where $X_i$ relates density at voxels through which a ray passes to a measured value of the ray that has passed through the item under inspection. Estimated voxel densities $\hat{\rho}_k$ are multiplied by $X_i$, which yields an estimate of values measured along the ith ray. By subtracting this estimate from the actual measured value $x_i$ an error value is obtained. When these error values are weighted by an uncertainty value $\sigma_i$, squared and summed with similarly computed values along other rays, a value of $M^2$ results. The iterative method aims to find density values ρ that minimize the changes in $M^2$ with respect to changes in density values. Density values that satisfy this criterion represent the computed image.

ART is only one many iterative reconstruction methods known in the art. Any of numerous iterative reconstruction techniques may be used instead of or in addition to ART. For instance, any of the following methods may be used: ordered-subsets maximum likelihood method (OSC), simultaneous algebraic reconstruction technique (SART), simultaneous iterative reconstruction technique (SIRT), least-squares QR method, expectation maximization (EM), ordered subsets expectation maximization (OSEM), convex method, and ordered subset convex method.

The inventors have appreciated that the use of iterative reconstruction methods allows for the use of sparse detector array designs that include fewer detectors than would be required for image reconstruction using direct reconstruction techniques such as filtered back projection. Conventional imaging systems often include an array with 10,000-250,000 individual detectors to provide oversampling of the data to resolve potential ambiguities, as discussed above. Although the cost of individual detector units may be relatively small compared to the cost of the inspection system as a whole, the large number of detectors typically used in such systems results in a detector array cost that is substantial.

The inventors have appreciated that rather than using a fully-populated array of contiguous rows of detectors, imaging systems that use iterative reconstruction techniques may use sparsely-populated arrays that take advantage of the properties of iterative reconstruction to compensate for the fewer number of detectors in the sparse detector array, thereby preserving image quality.

Figure 3:
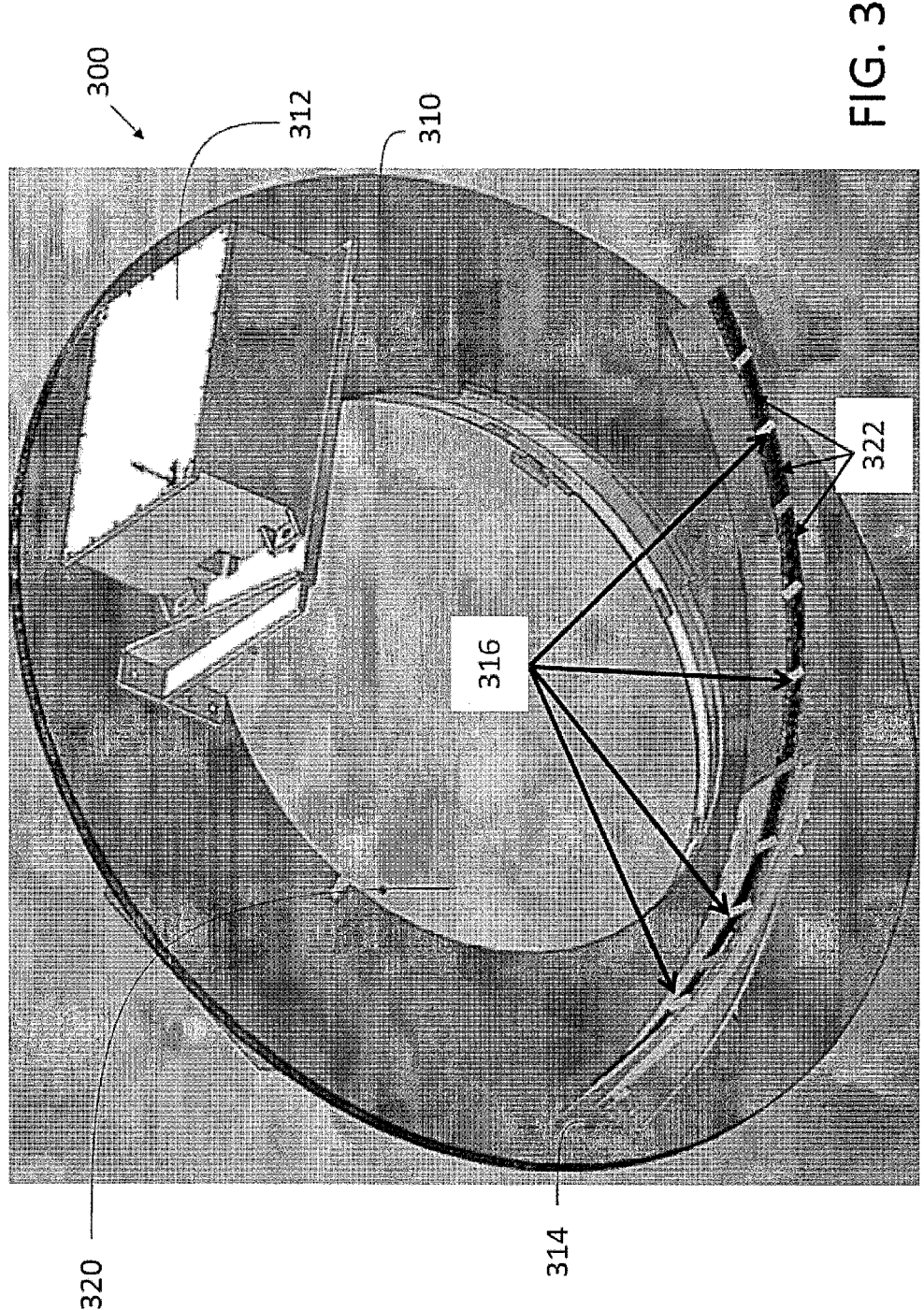
FIG. 3 illustrates a portion of an inspection system with a sparse detector array, in accordance with some embodiments of the present disclosure.

FIG. 3 illustrates a cross-section schematic of an exemplary inspection system 300 in accordance with some embodiments of the invention. Inspection system 300 includes a rotatable gantry 310 on which is mounted an x-ray source 312 and a sparse detector array 314 positioned opposite the x-ray source 312. Sparse detector array 314 comprises a plurality of rows 316 of detector elements configured to receive the x-ray radiation emitted from x-ray source 312, as described above. Each row 316 of the sparse detector array may include a plurality of detector elements oriented at an angle with respect to gantry 310. As shown in FIG. 3, the rows 316 of detector elements are oriented at a 90° angle to gantry 310 such that the detector elements are substantially parallel to a conveyor (not pictured) that carries an object though an inspection area located within gantry bore 320 of inspection system 300. Although x-ray source 312 and sparse detector array 314 are illustrated as being mounted in a substantially circular arc orientation on gantry 310, it should be appreciated that any suitable orientation for x-ray source 312 and sparse detector array 314 may alternatively be used and embodiments of the invention are not limited in this respect.

At least some of the rows 316 of sparse detector array 314 may be separated by gaps 322 such that the number of detectors in sparse detector array 314 is less than the number of detectors in a full detector array having contiguous rows of detectors. One constraint of direct reconstruction methods, described above, is that they often require a full array of contiguous detectors to accurately determine an image of an item under inspection. However, the inventors have recognized and appreciated that iterative reconstruction methods may compensate for the fewer radiation measurements collected using a sparsely-populated detector array. This realization is contrary to many conventional image processing systems that often include large numbers of detectors to provide oversampling, as discussed above.

The sparsity of sparse detector array 314, determined as a percentage of rows 316 in the sparse detector array 314 compared to a full array of detectors is preferably less than 50% in accordance with some embodiments, although any suitable sparsity for sparse detector array 314 may be used. For example, some embodiments may include a sparse detector array 314 having a sparsity less than 25%. By reducing the number of rows 316 in sparse detector array 314, the cost of inspection system 300 may be reduced.

In some embodiments, the spacing between rows 316 in sparse detector array 314 may be uniform along the sparse detector array 314, although in other embodiments, the spacing between rows 316 may vary along sparse detector array 314. The inventors have recognized that it may be advantageous in some embodiments to reduce the spacing between rows 316 in the center of sparse detector array 314 to provide more detector coverage, whereas rows 316 at the edges of sparse detector array 314 may be spaced farther apart, as discussed in more detail below. For example, in embodiments where rows 316 of sparse detector array 314 are arranged in a substantially circular arc, the middle of the arc may be populated with contiguous rows of detectors, whereas the outer edges of the arc may be populated with non-contiguous rows of detectors. It should be appreciated, however, that the particular spacing of rows 316 in sparse detector array 314 is not a limitation of embodiments of invention and the spacing may depend, at least in part, on the imaging requirements of a particular implementation.

In some embodiments, x-ray source 312 and/or associated electronics, including a power supply, may be mounted on gantry 310 in a housing as illustrated in FIG. 3. In some embodiments, the size of inspection system 300 may be reduced by configuring the shape of the power supply and/or housing to conform to the structure of the gantry 310. For example, rather than using a rectangular housing as illustrated in FIG. 3, the shape of the housing may be configured to be more circular to allow the size of inspection system 300 to be more compact.

Figure 4:
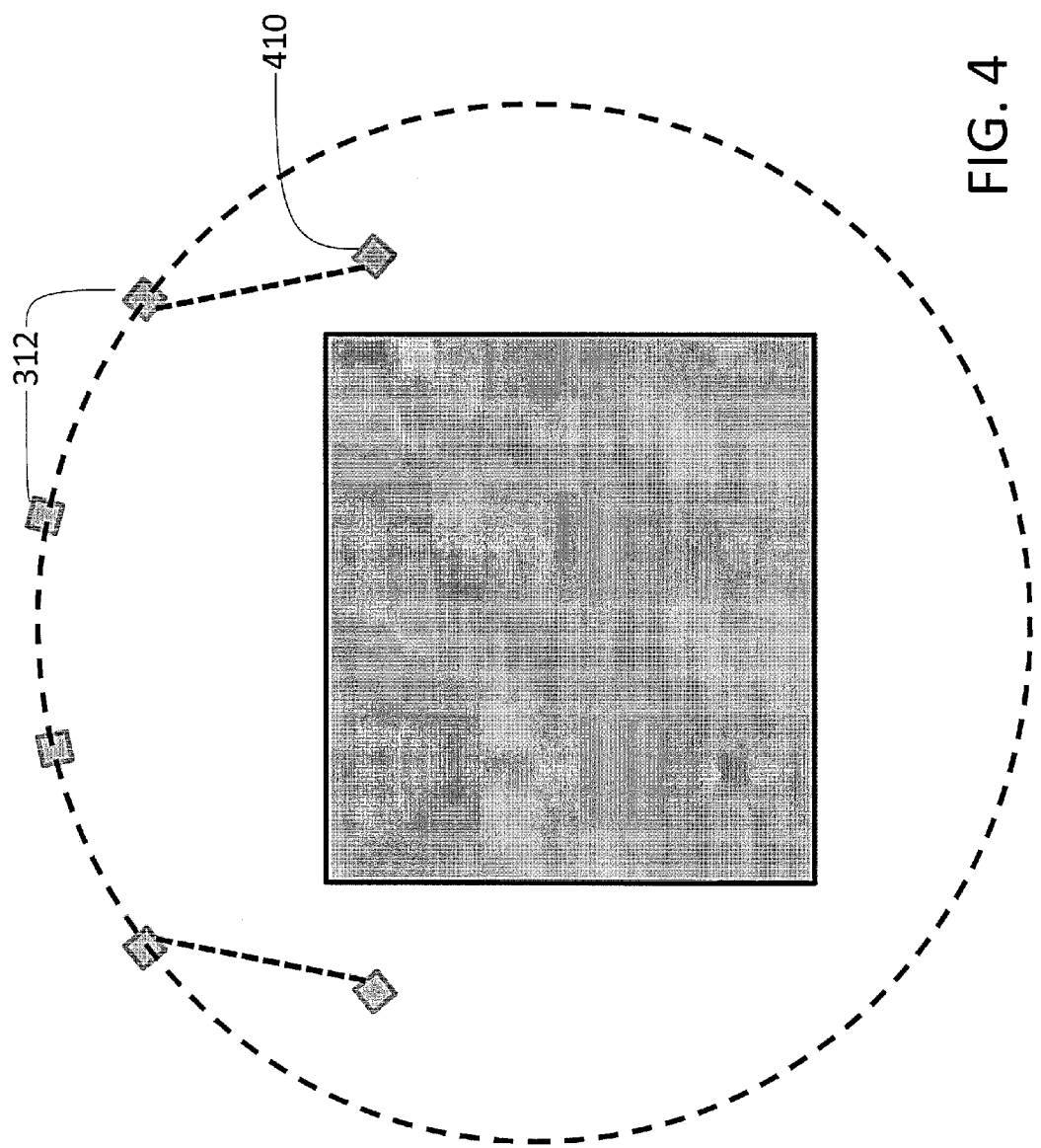
FIG. 4 illustrates a schematic of a cross section of a portion of an inspection system including at least one wing detector row as part of a sparse detector array, in accordance with some embodiments of the present disclosure.

FIG. 4 illustrates a cross section through an additional orientation of rows 316 in a sparse detector array designed to further reduce the size of inspection system 300. The sparse detector array in FIG. 4 includes at least some "wing" detector rows 410 mounted inward of the substantially-circular arc of the main set of detectors. Such sparse detector array arrangements may reduce the diameter of circumscription as rotating gantry 310 rotates thereby enabling a more compact design of inspection system 300. Although FIG. 4 illustrates a sparse detector array with two wing detector rows 410, it should be appreciated that any suitable number and orientation of wing detector rows 410, including a single wing detector row, may alternatively be used and embodiments of the invention are not limited in this respect.

Figure 5:
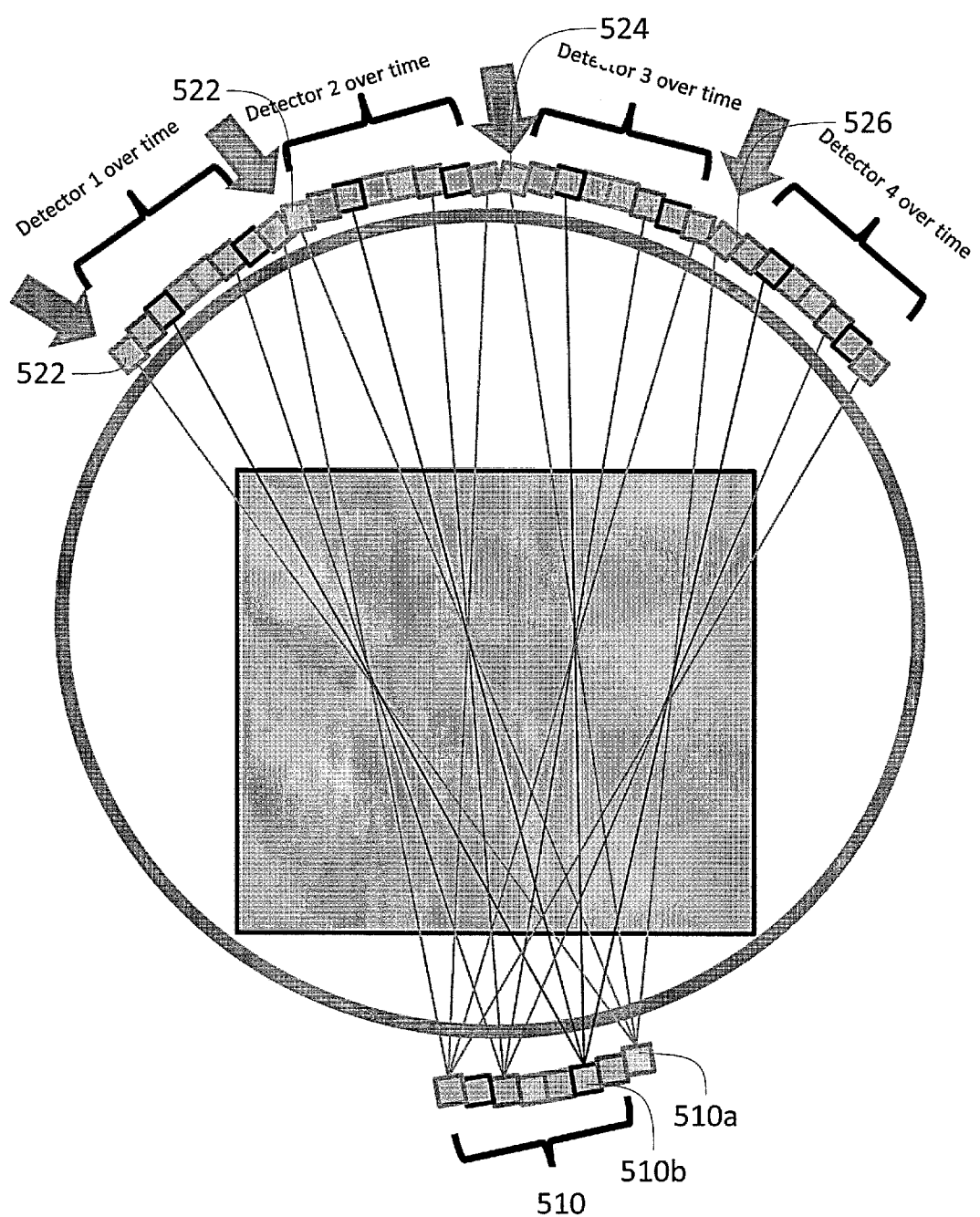
FIG. 5 illustrates a schematic of a cross section of a portion of an inspection system, in accordance with some embodiments of the present disclosure.
Figure 6:
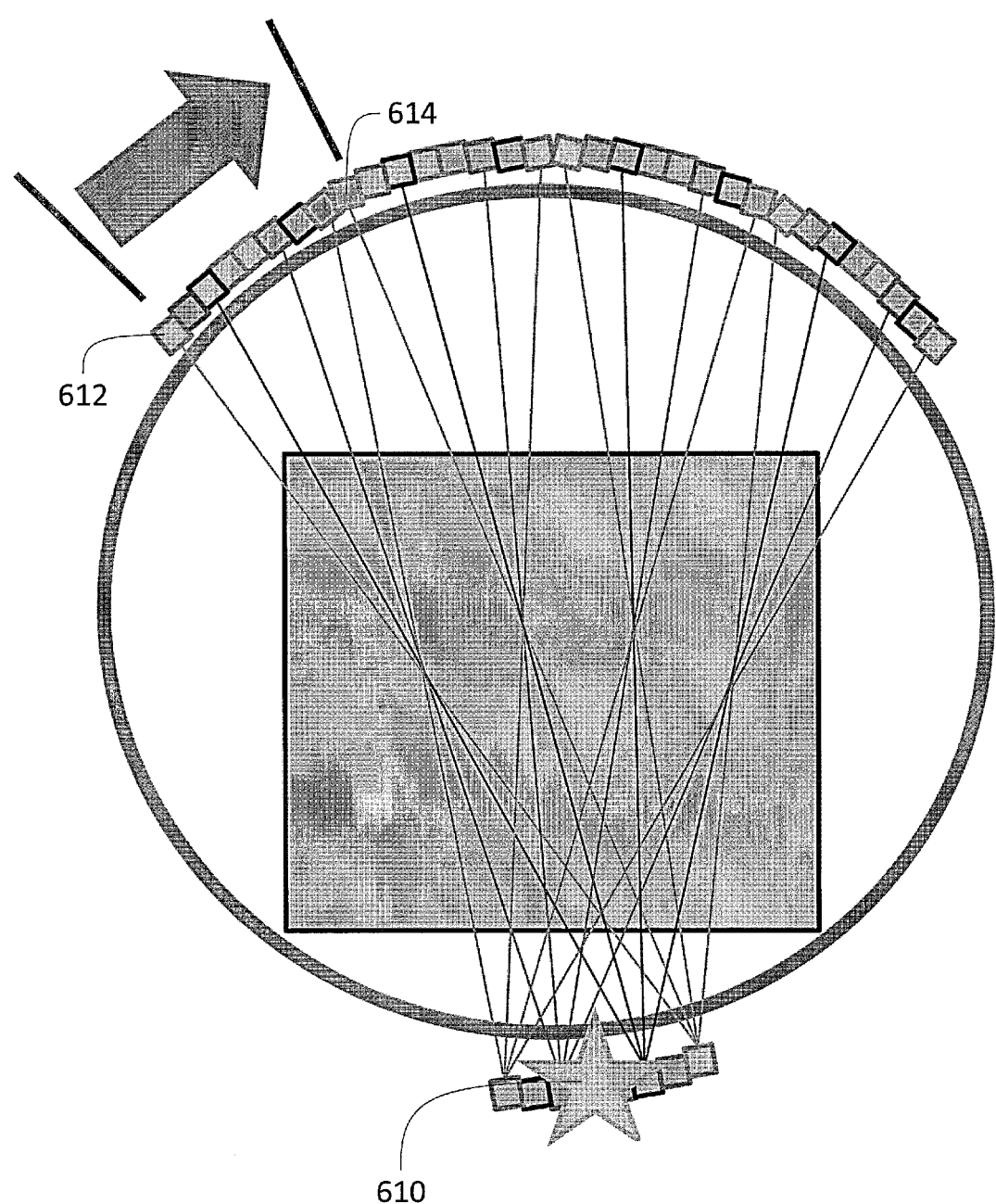
FIG. 6 illustrates a schematic of a cross section of a portion of an inspection system including a supersource at a first position, in accordance with some embodiments of the present disclosure.

FIG. 5 illustrates the operation of some embodiments of the invention employing a sparse detector array. In the example of FIG. 5, an x-ray source emits rays of radiation at multiple timepoints as the x-ray source and sparse detector array mounted on a rotating gantry rotates around an object to be imaged. The exemplary source emits a fan-beam of x-ray radiation that includes rays covering an angular extent (e.g., 60°) of the sparse detector array. The exemplary sparse detector array shown in FIG. 5 includes four detectors 520, 522, 524, and 526. During a first data acquisition (t=0), the detectors are located at the positions indicated by the arrows in FIG. 5 and the source is located at position 510a. X-rays emitted by the source pass through object 500 and impinge on the detectors. After data is acquired at time t=0, the gantry is rotated (thereby rotating the source and the detectors) and a second data acquisition is obtained at time t=1 indicated by source position 510b. This process is repeated until all of the detector positions have been sampled. The detectors in the exemplary sparse detector array of FIG. 5 are illustrated as being widely spaced merely to illustrate an operation of some embodiments of the invention and a sparse detector array with any suitable sparsity may alternatively be used.

The inventors have appreciated that the data acquisition time per source-detector ray may be reduced relative to that in a fully-contiguous detector array. Data acquisition may be increased in accordance with some embodiments of the invention because all data acquisitions may be grouped together to form a "filled-in set" of data from the time it would have taken a detector 612 to move from its initial position to the initial position of the next detector 614 in the sparse detector array.

Figure 7:
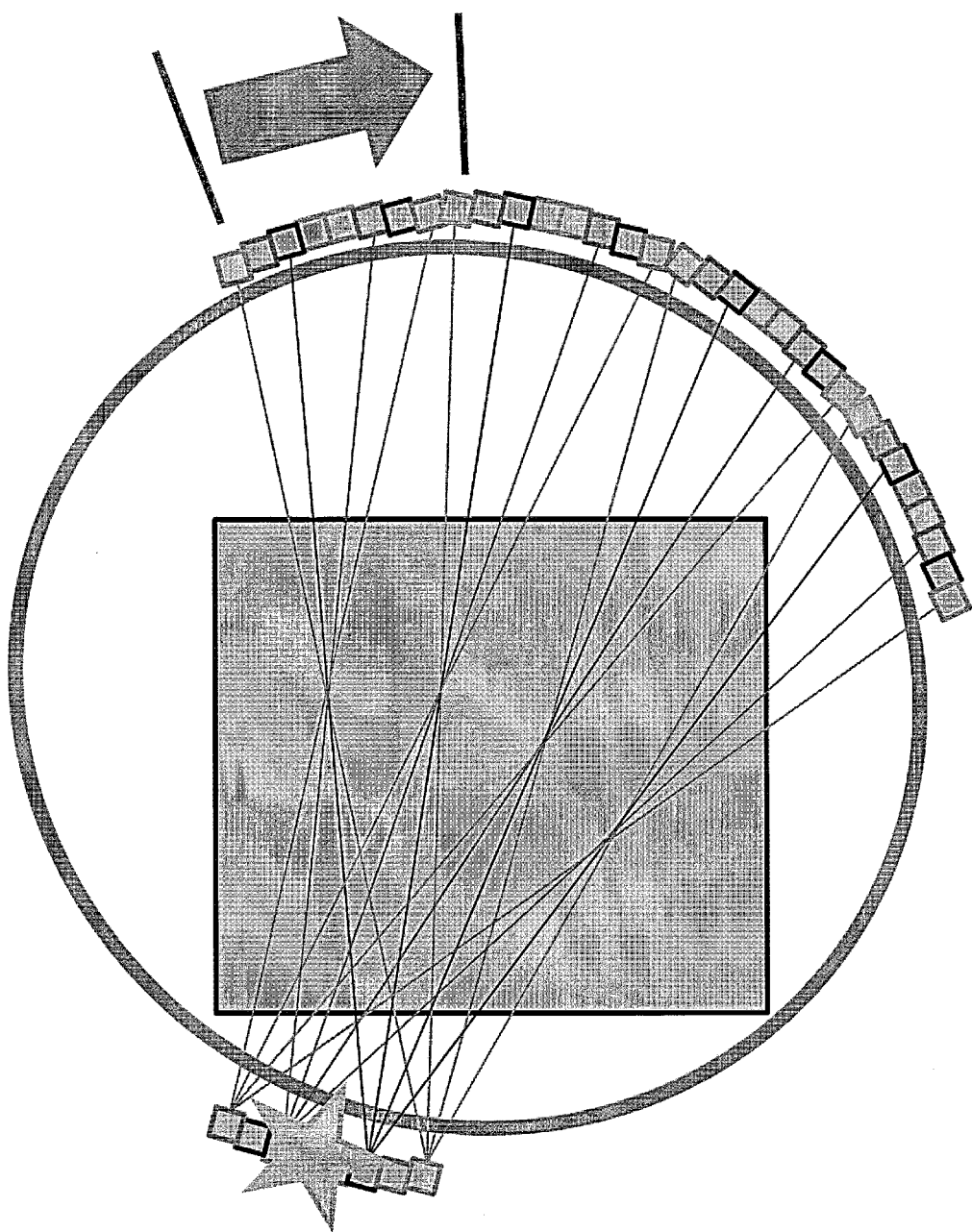
FIG. 7 illustrates a schematic of a cross section of a portion of the inspection system of FIG. 6 including a supersource at a second position, in accordance with some embodiments of the present disclosure.
Figure 8:
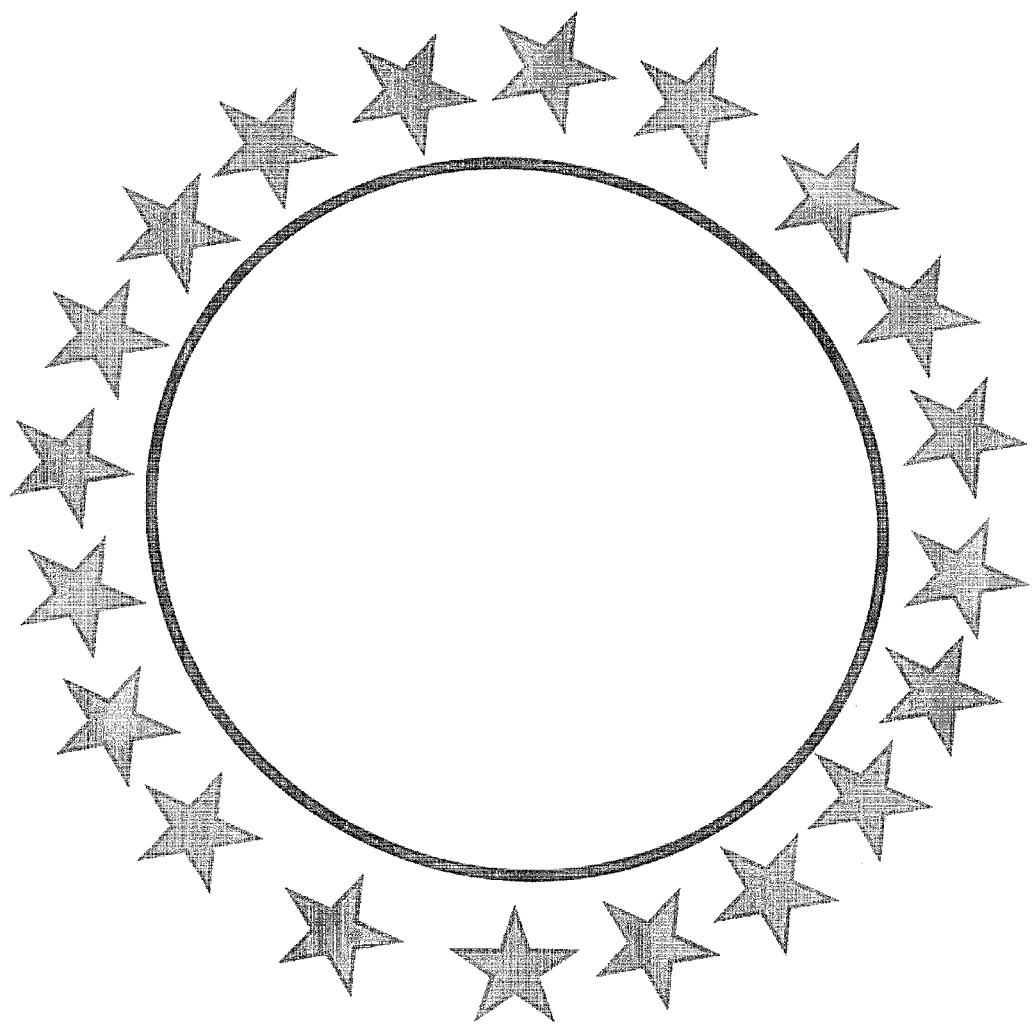
FIG. 8 illustrates a schematic of a cross section of a portion of an inspection system including a plurality of supersource positions, in accordance with some embodiments of the present disclosure.

After data is acquired corresponding to a filled-in set, the source may be moved to a new position (e.g., by rotating the gantry on which the source is located) as illustrated in FIG. 7 and a new filled-in set of radiation measurements may be acquired. This process may be repeated until data acquisition for the object has been completed in accordance with a particular imaging protocol. For example, if an imaging protocol instructs the inspection system to acquire data while rotating the source 360° around the object to be imaged, twenty filled-in sets of data may be required to acquire data for one full rotation as illustrated in FIG. 8. The number of such sets used for data acquisition may depend, at least in part, on the sparsity of the sparse detector array.

Figure 9B:
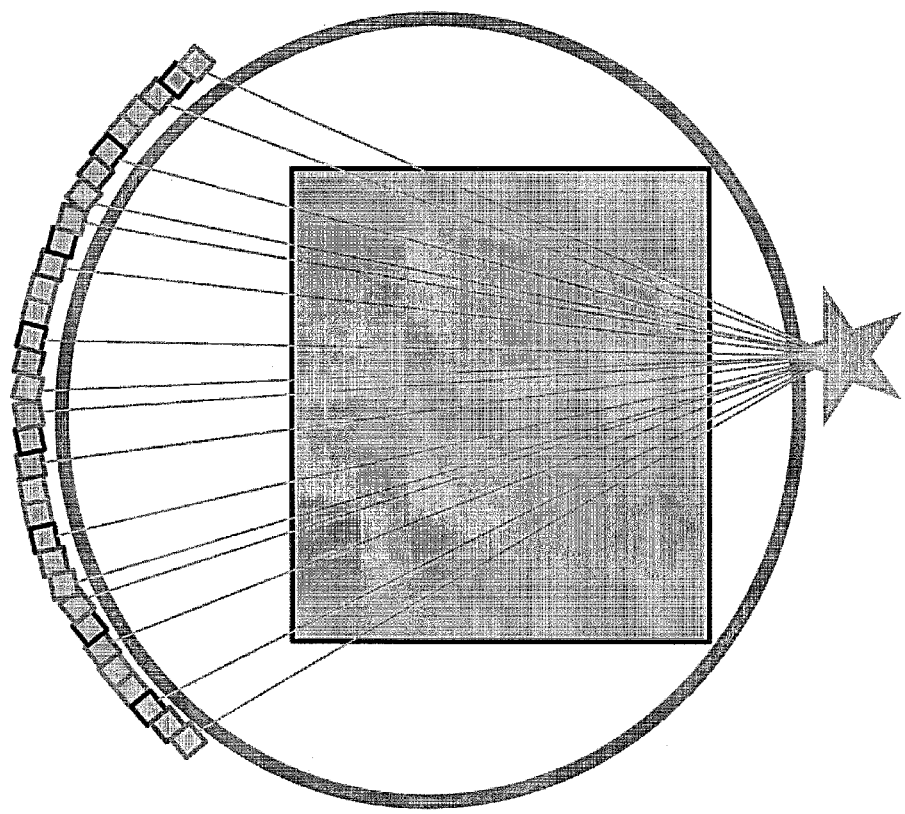
FIGS. 9A and 9B illustrate a comparison of simulated x-ray patterns for a supersource with a sparse detector array, in accordance with some embodiments of the present disclosure and a supersource with a full detector array.
Figure 9A:
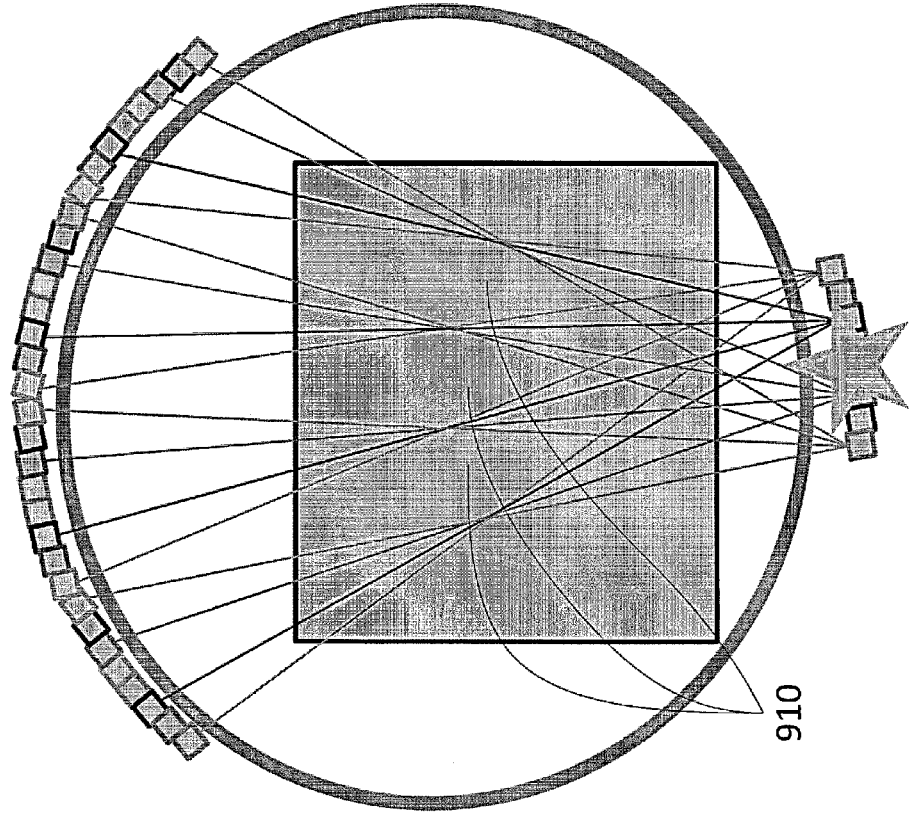
Figure 10A:
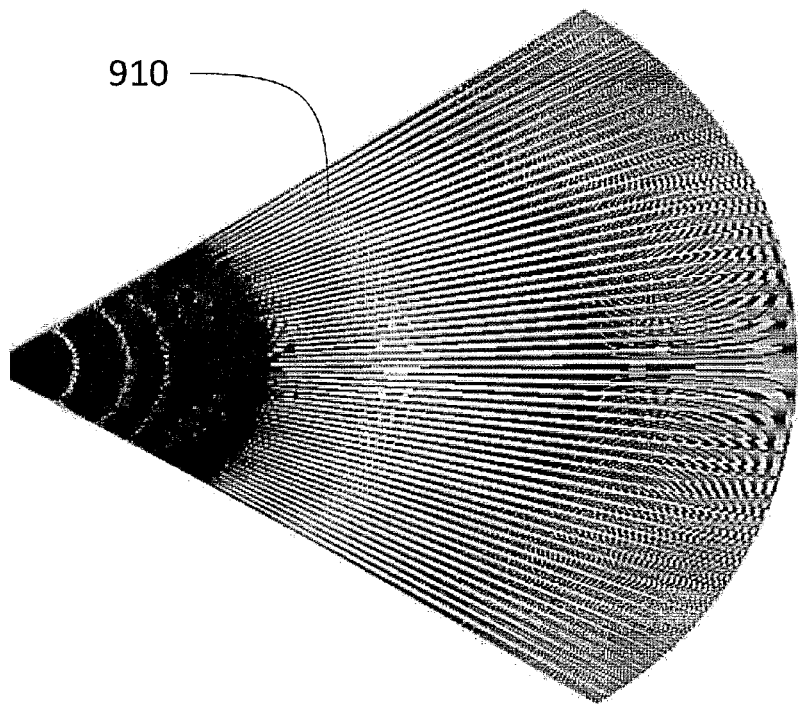
FIGS. 10A and 10B illustrate simulated ray patterns for an first inspection system having reduced x-ray coverage at a portion of an inspection area, in accordance with some embodiments of the present disclosure.
Figure 10B:
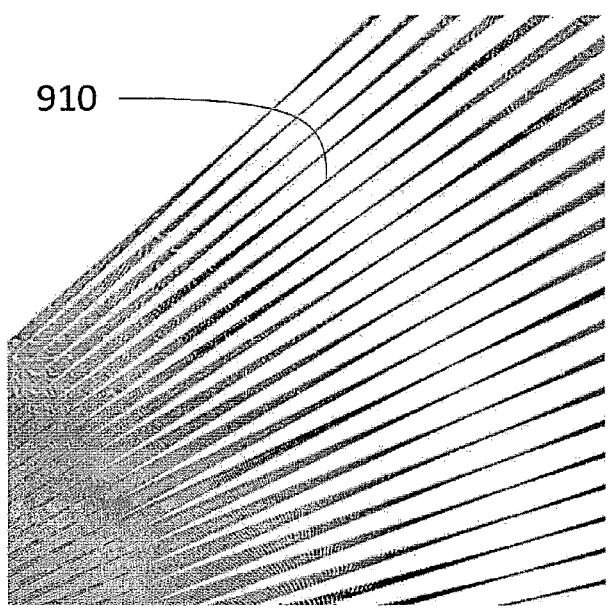

FIGS. 9A and 9B illustrate an exaggerated comparison between a simulated ray pattern for an inspection system with a full set of detectors (FIG. 9B) and a simulated ray pattern for an inspection system with a sparse detector array (FIG. 9A), in accordance with some embodiments of the invention. Although the ray count between the two systems and the angular coverage of the two systems is similar, the sparse detector array system in FIG. 9A illustrates portions 910 of the inspection area through which rays do not pass resulting in portions of the object that are not imaged effectively. FIG. 10A illustrates a simulated ray pattern for a sparse detector array having a sparsity of 12.5%. As can be observed in FIG. 10A, and more clearly in FIG. 10B, which represents an enlarged portion of FIG. 10A, as the source position is varied, the portion 910 of the inspection area not effectively imaged may form a ring at the isocenter of an inspection area situated between a source and the sparse detector array. As further illustrated in FIG. 10A, other portions of the inspection area may also receive incomplete ray coverage, albeit to a lesser extent.

The inventors have appreciated that for many security applications in which some embodiments of the invention are designed to be employed, incomplete imaging coverage of an object is unacceptable. Accordingly, the inventors have recognized ways to mitigate the incomplete coverage of portions of the object near the isocenter inspection area. In some embodiments, rather than using a sparse detector array in which the spacing between the detectors is uniform, the center of the sparse detector array may be more densely populated with detectors to more effectively cover the isocenter region of the object. For example, in one implementation having a sparse detector array with an angular extent of 60°, the central 1° of the array may include contiguous detector rows to more effectively cover the isocenter portion of the inspection area. Such an increase in the number of detectors is likely to be minimal compared to the potential benefits of increased coverage.

Figure 11:
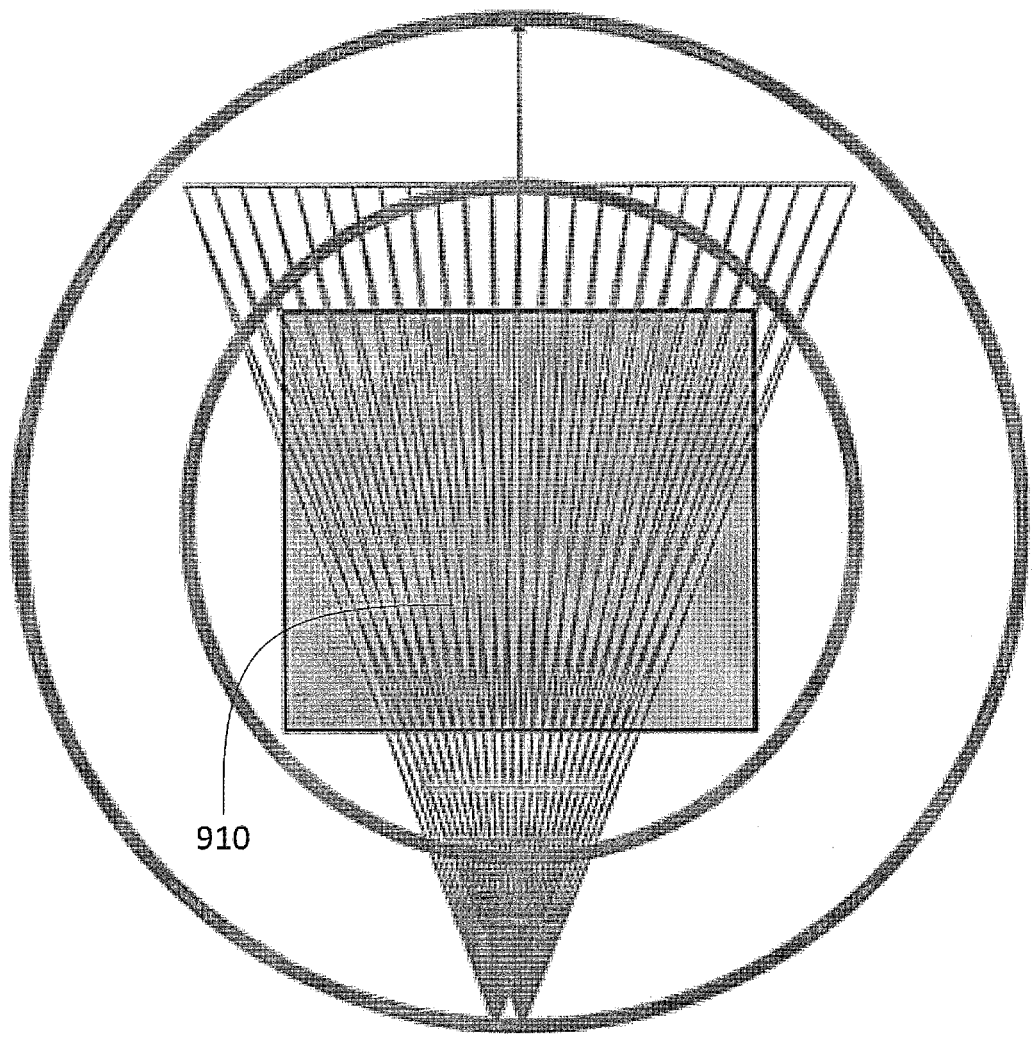
FIG. 11 illustrates a simulated ray pattern for a second inspection system having reduced x-ray coverage at a portion of an inspection area, in accordance with some embodiments of the present disclosure.

An alternative embodiment in which the detectors remain stationary, but the sources rotate on the gantry may also help mitigate the incomplete coverage of some embodiments of the invention. Simulated ray patterns for such a system is illustrated in FIG. 11. As can be seen from FIG. 11, the region of incomplete coverage 910 of the inspection area, while still present, may be reduced relative to the simulated ray pattern shown in FIG. 10.

Another alternative embodiment arranges the components of the inspection system such that most objects inspected by the inspection system will be less affected by incomplete coverage at the isocenter of the inspection area. This may be accomplished, in part, by positioning the tunnel including the conveyor low in the gantry bore. The inventors have recognized that many objects imaged in an x-ray system, for example, at a security checkpoint, are low-profile items that reside close to the conveyor belt. Accordingly, if the conveyor is located low in the gantry bore, the incomplete isocenter coverage areas may occur primarily above the imaged object rather than within the imaged object. It should be appreciated that any combination of the above-described methods, and others, may be used to mitigate the effects of incomplete coverage of an inspection region and aspects of embodiments of the invention are not limited in this respect.

Additional variations to some embodiments of the invention for particular applications are also contemplated. For example, in some embodiments the rows of the sparse detector array may be oriented parallel to the moving direction of a conveyor that transports an object through an inspection area for imaging. However, in other embodiments, the orientation of the detector rows may be angled relative to the moving direction of the conveyor either with or against the spiral direction of imaging. For example, in one implementation, the detector rows may be oriented to cross the moving conveyor direction at an angle of # detectors/sparsity of the detector array.

The inventors have recognized that it may be advantageous in different implementations to use different numbers of sources in embodiments of the invention. For example, in some embodiments described above, a single source may be used to emit radiation across an angular extent (e.g., 60°) covering all detectors in a sparse detector array. In other embodiments, multiple sources may be used to emit radiation on different portions of the sparse detector array either simultaneously or in succession.

Additionally, different types of sources may be used in various embodiments of the invention. For example, in one implementation for high-resolution imaging, the x-ray source may comprise a plurality of carbon nanotube elements that each act as an individual source activated by applying in time-sequence a signal to each of the elements. Because triggering of the carbon nanotube elements may be instantaneous, the resolution of conventional volumetric images as an object is transported through an inspection area may be improved.

In other embodiments, the x-ray source may comprise a distributed array of switchable x-ray sources that, when activated in time-sequence, emit x-ray radiation. The switchable x-ray sources in the distributed array may be activated by application of any suitable signal to each source including, but not limited to, a voltage and a light source.

In other embodiments, the x-ray source may comprise a multi-energy x-ray source that emits x-ray radiation at more than one energy level. For example, the inspection system may include one or more X-ray generation subsystems adapted to generate X-ray radiation at a first energy level and a second energy level. Alternatively, a multi-energy x-ray source may emit x-ray radiation at more than two energy levels. To support multi-energy imaging, each X-ray generation subsystem may generate radiation of a different energy level during successive intervals when it operates. By correlating the detector outputs to times in which the X-ray generation subsystems are generating, for example, high- and low-energy X-rays, high and low X-ray data may be collected for a multi-energy image analysis. Such an analysis may be performed using techniques as known in the art or in any other suitable way.

In other embodiments employing a multi-energy x-ray source, at least some of the detectors in the sparse detector array may be configured to classify received x-ray radiation as having one of a plurality of energies, such as a first energy or a second energy. For example, some or all of the detectors in the sparse detector array may be adapted to record individual x-ray photon arrival energies with sufficient resolution to separate photons having a first energy from photons having a second energy. The detectors may be configured to classify the energy of received x-ray radiation by, for example, being constructed of a material, such as CdZnTe (CZT) that enables the classification of individual photons. Such detectors are known in the art and are often commonly referred to as photon-counting detectors or multispectral detectors.

In other embodiments, a stationary x-ray source with a plurality of sequential time-multiplexed source positions may be used. An example of such a stationary x-ray source is an e-beam. In e-beam imaging systems, one or more e-beams are directed to impinge on the surface of a target responsive to the e-beams. The target may be formed from, for example, tungsten, molybdenum, gold, or other material that emits X-rays in response to an electron beam impinging on its surface. For example, the target may be a material that converts energy in the e-beam into X-ray photons, emitted from the target essentially in the 4π directions. The released energy may be shaped or collimated by blocking selected portions of the X-rays emitted from the target using any of various radiation absorbing material (such as lead). For example, the X-ray may be collimated to form a cone beam, a fan beam, a pencil beam or any other X-ray beam having generally desired characteristics. The collimated X-rays may then pass into an inspection region to penetrate an object of interest to ascertain one or more characteristics of the object.

While conventional X-ray scanning systems employ one or more sources and detectors positions or rotated in a circular geometry, e-beam imaging systems may comprise arbitrary, and more particularly, non-circular geometries, which offers a number of benefits with respect to the flexibility of the design and may facilitate more compact and inexpensive X-ray detection system. Applicant has identified and developed various e-beam techniques for use in arbitrary geometry systems that facilitate relatively inexpensive, compact and efficient X-ray detections systems.

In one exemplary X-ray scanning system, X-rays may be generated by directing an e-beam along a target via a scanning path that includes at least one substantially circular portion and at least one non-circular portion. The system includes a scanning path having a plurality of substantially linear portions and a plurality of substantially circular portions. For example, the scanning path may traverse a substantially rectangular U-shaped target formed from three substantially linear segments connected by substantially circular segments.

In another exemplary X-ray scanning system, the target which converts energy in an e-beam to X-ray energy may be provided as a plurality of segments. In one exemplary configuration, the target comprises at least one substantially circular segment and at least one substantially linear segment. In some embodiments, the plurality of segments are provided continuously. In other embodiments, at least one of the plurality of segments is provided discontinuous with at least one other segment. For example, each segment may be offset in a direction parallel to the direction of conveyance of an item being inspected by the X-ray scanning system.

Figure 12:
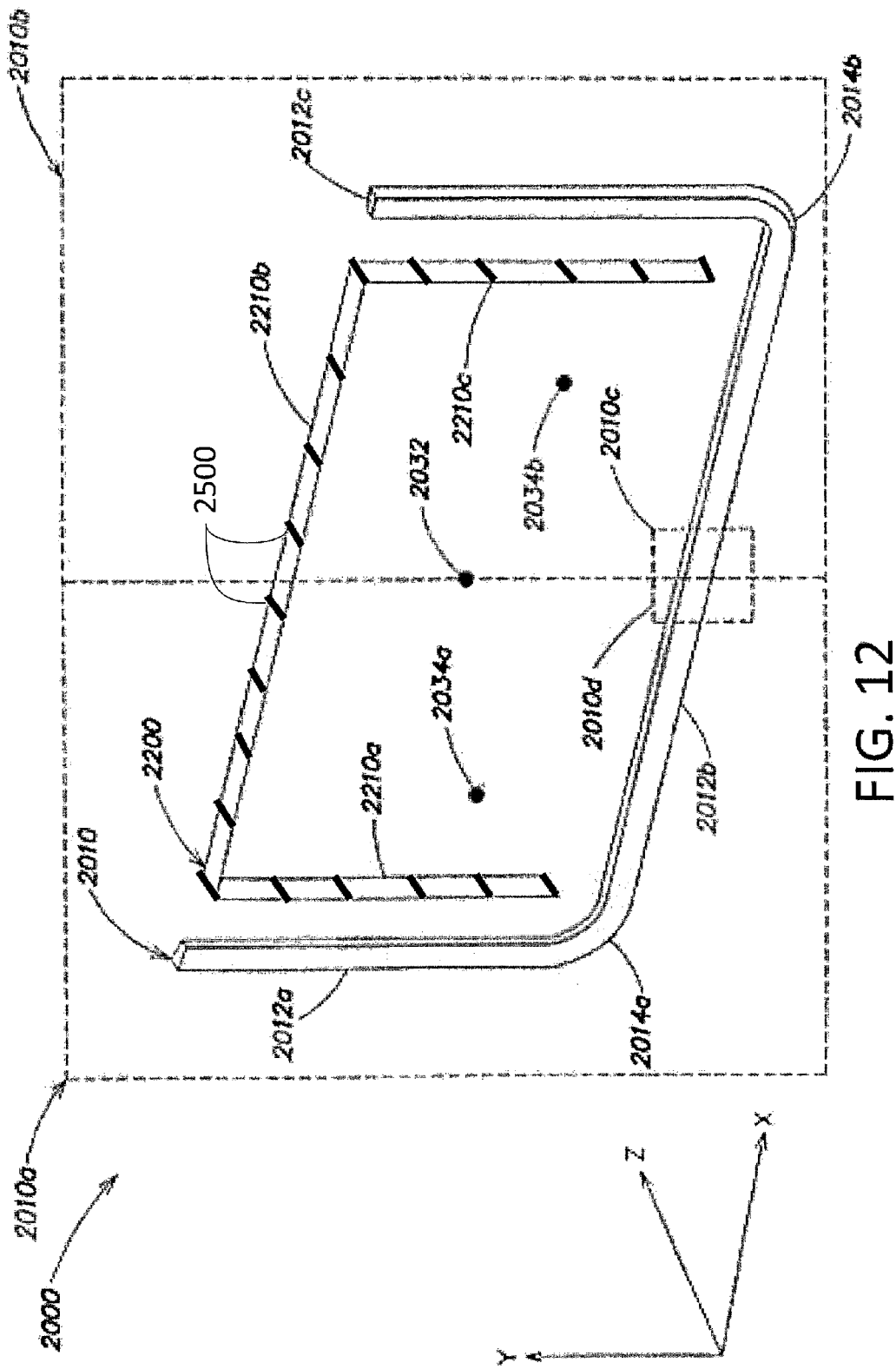
FIG. 12 illustrates an arbitrary geometry target and a detector using e-beam technology, in accordance with some embodiments of the present disclosure.
Figure 13:
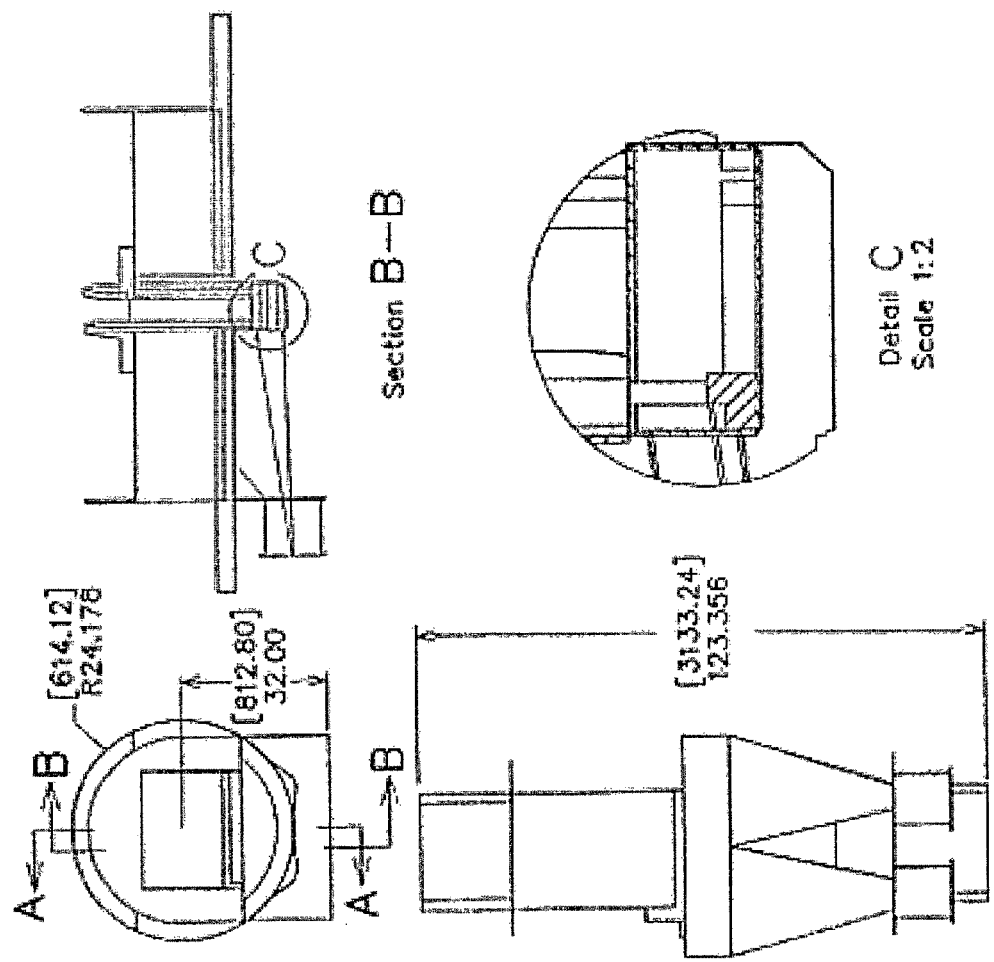
FIGS. 13-21 illustrate various portions of an x-ray scanning system using dual, steered electron beam radiation sources, in accordance with various embodiments of the present invention.
Figure 13:
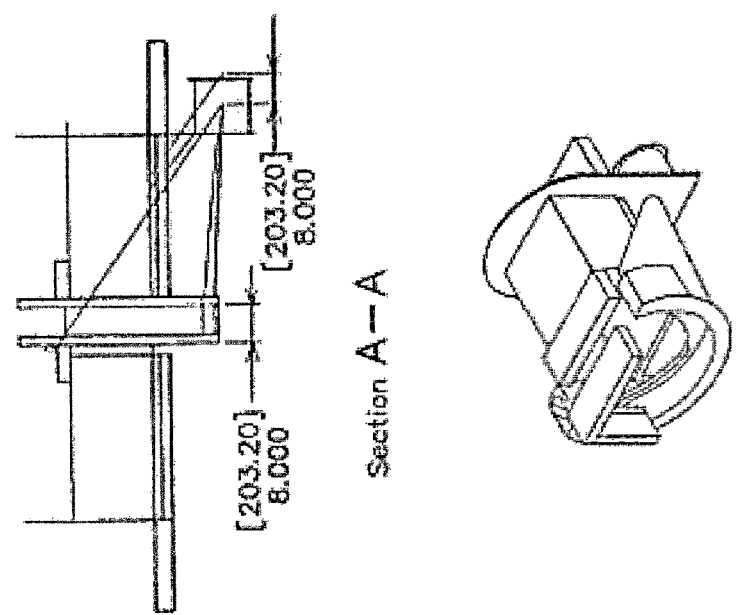
Figure 14:
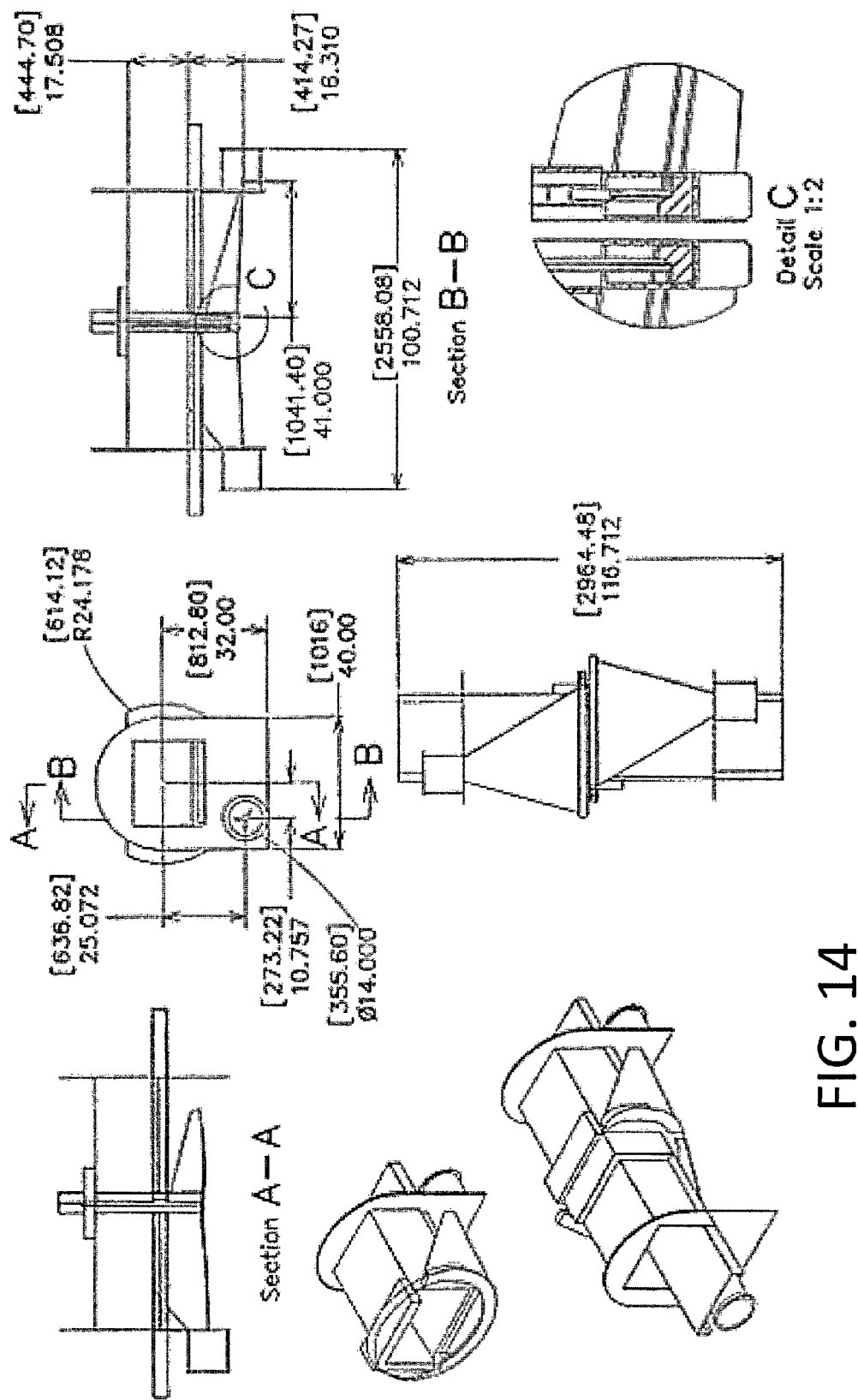
Figure 15:
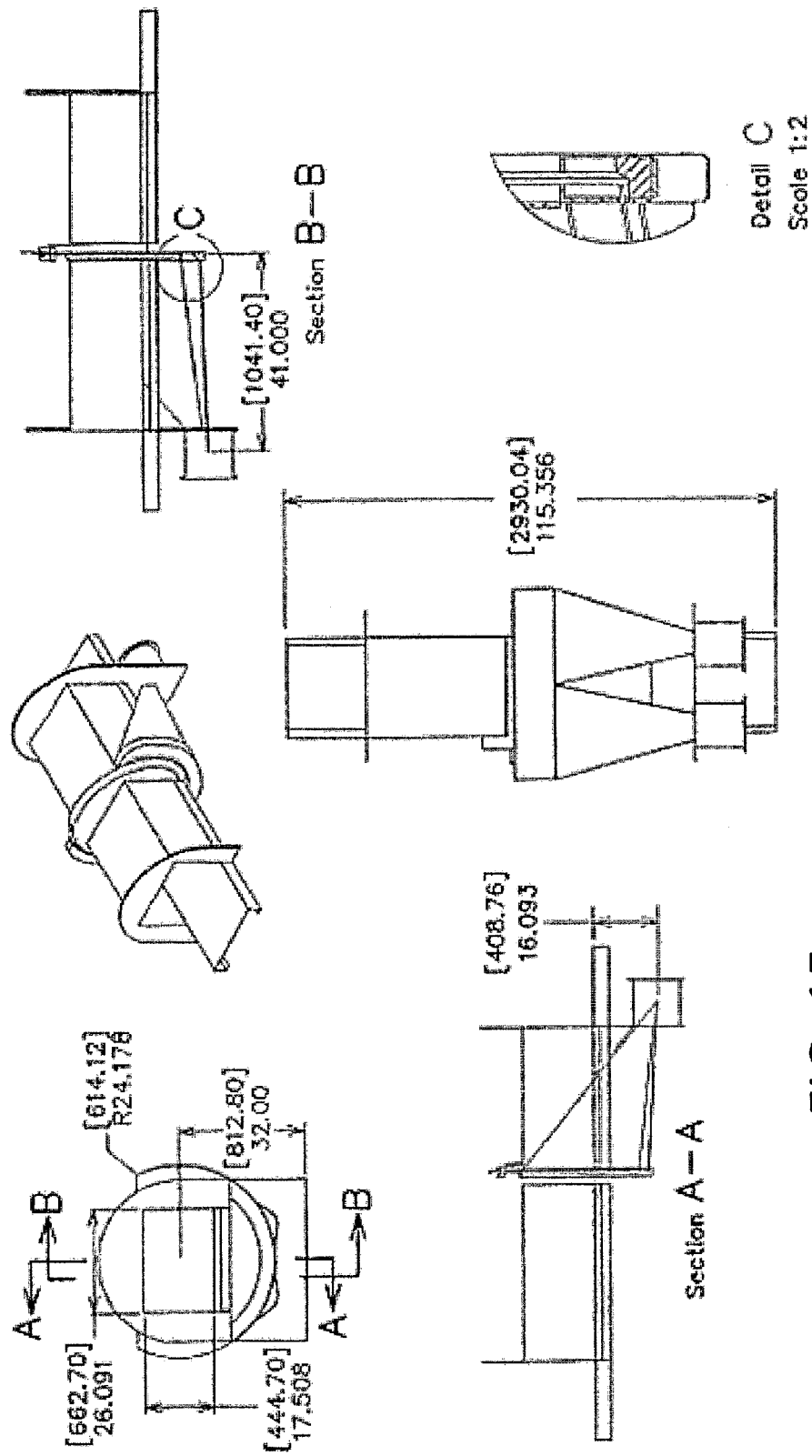
Figure 16:
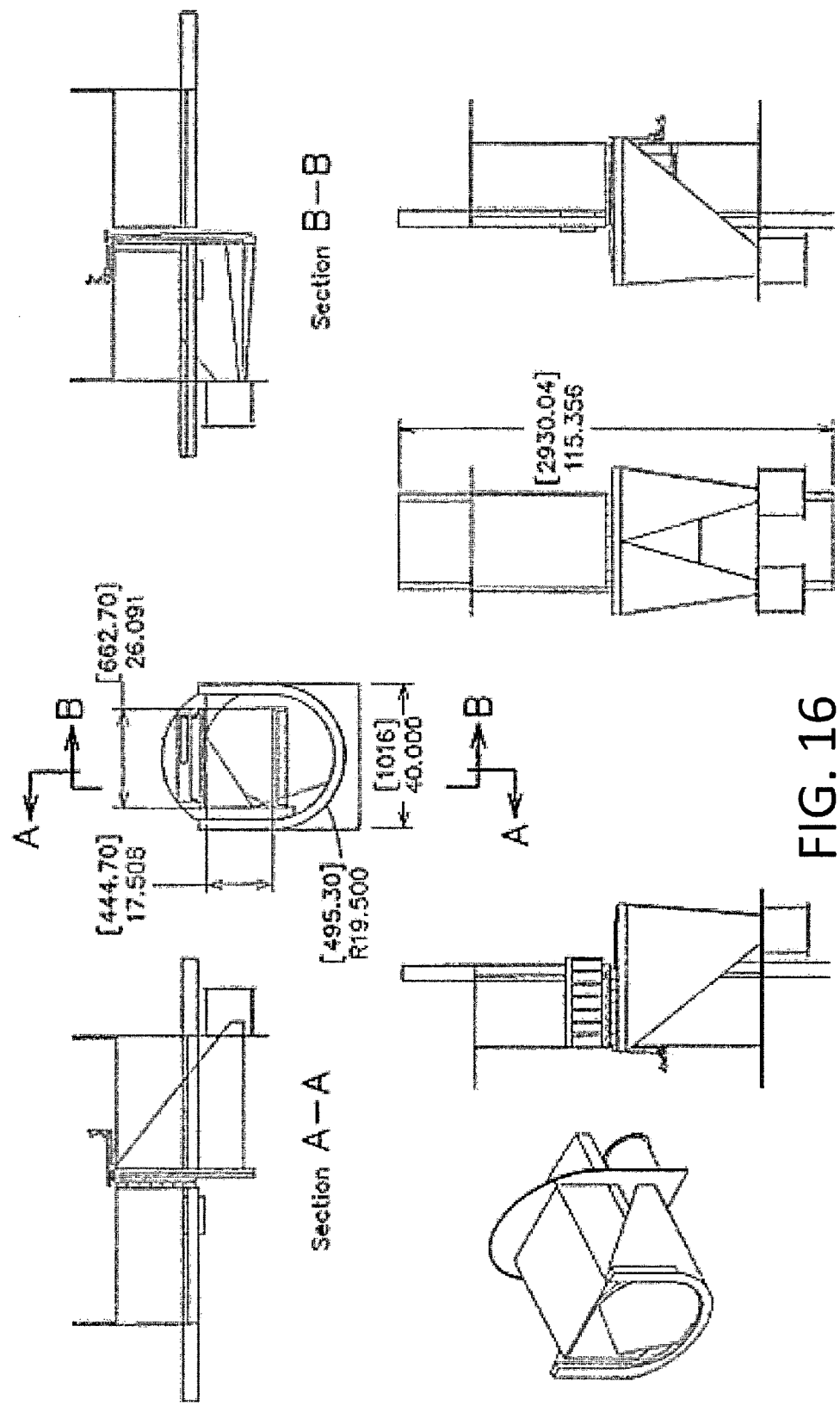
Figure 17:
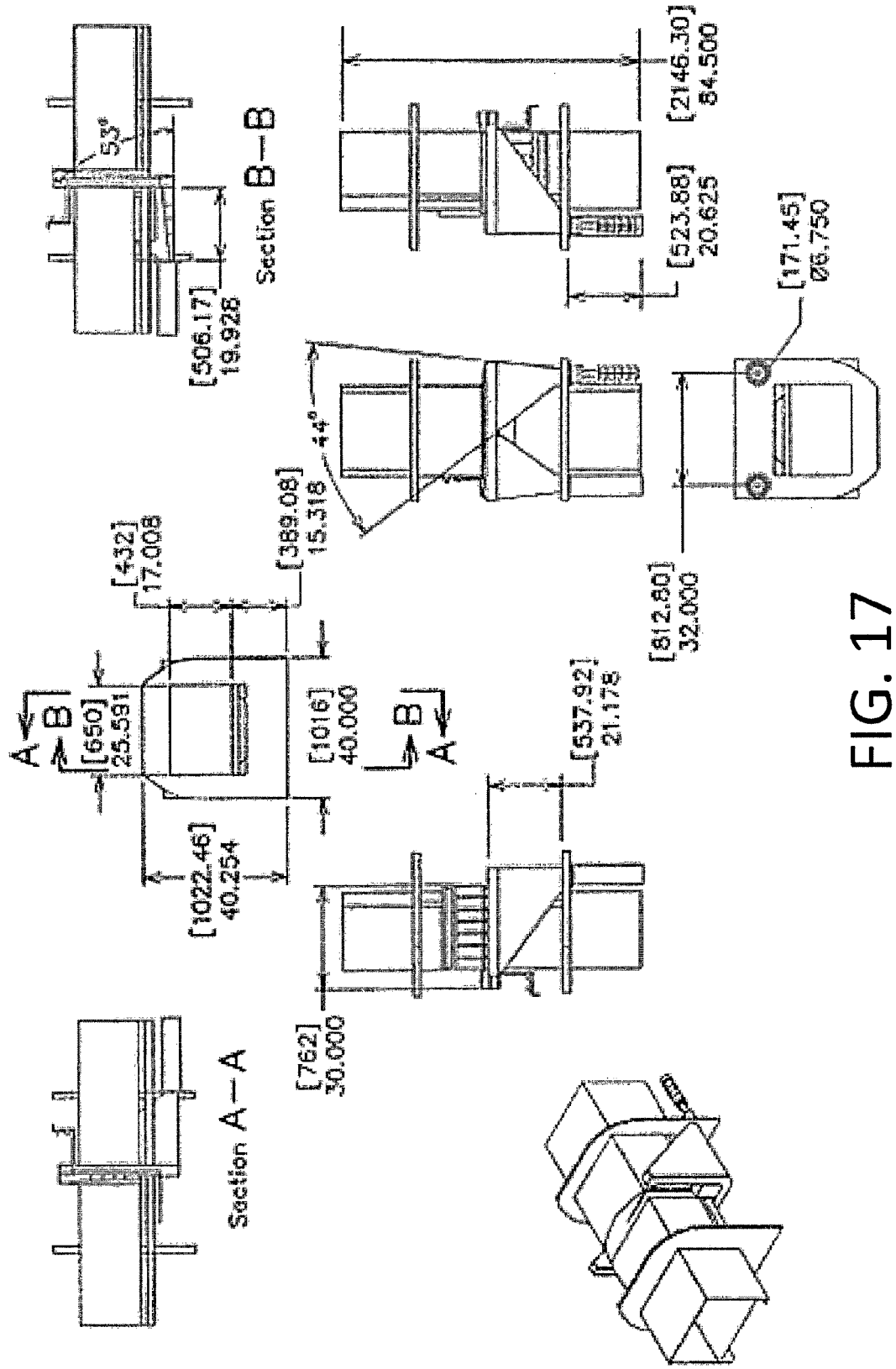
Figure 18:
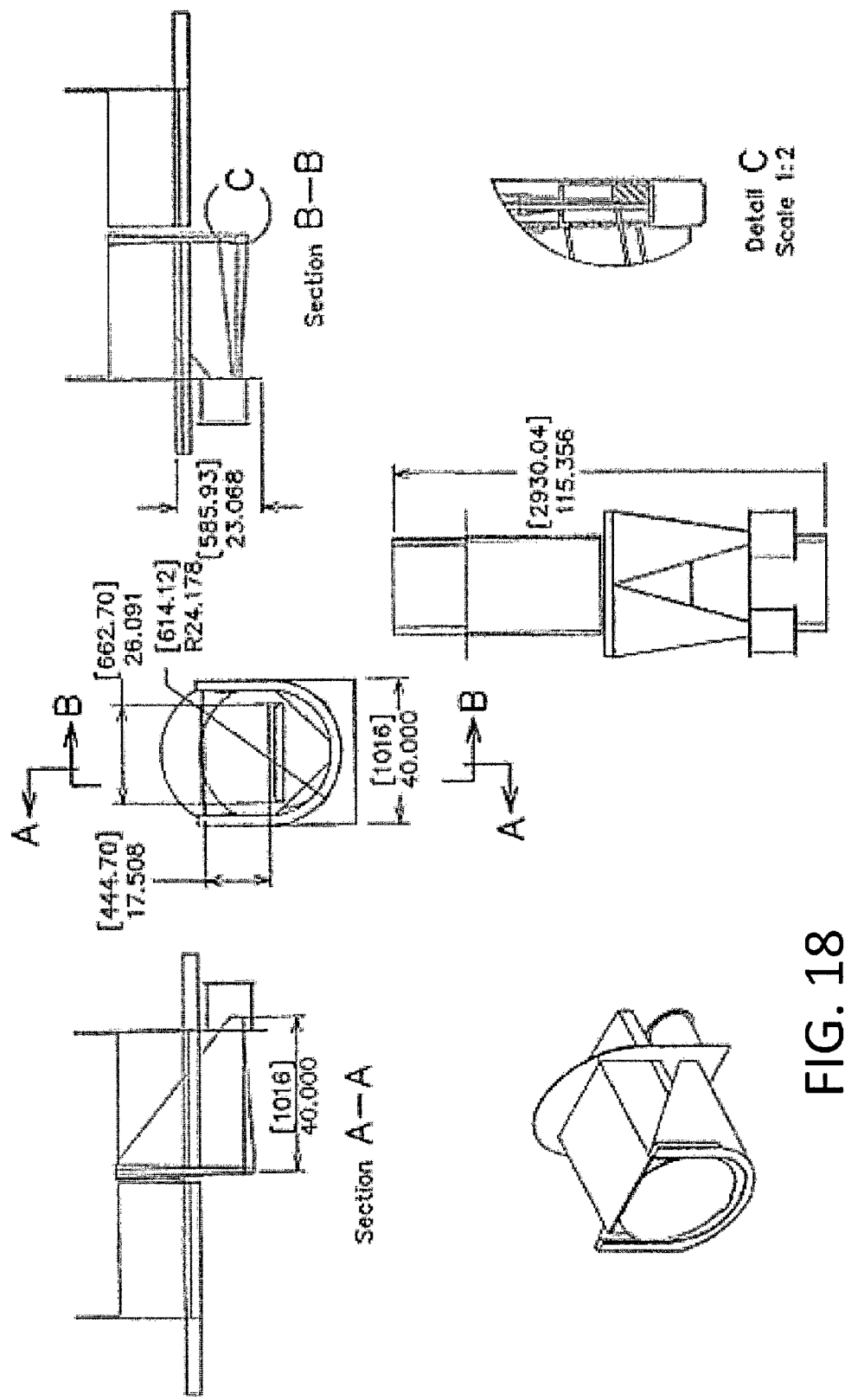
Figure 19A:
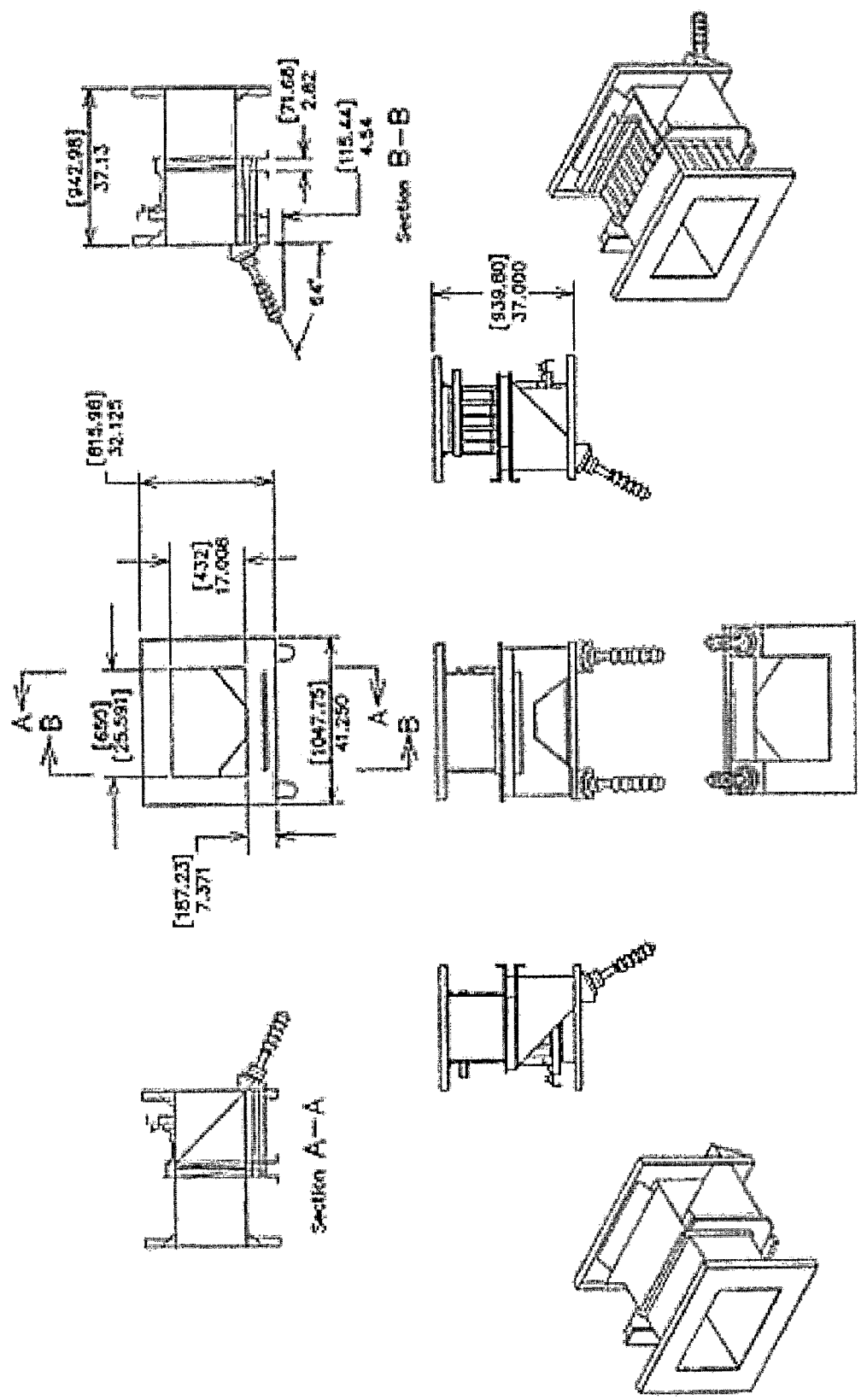
Figure 19D:
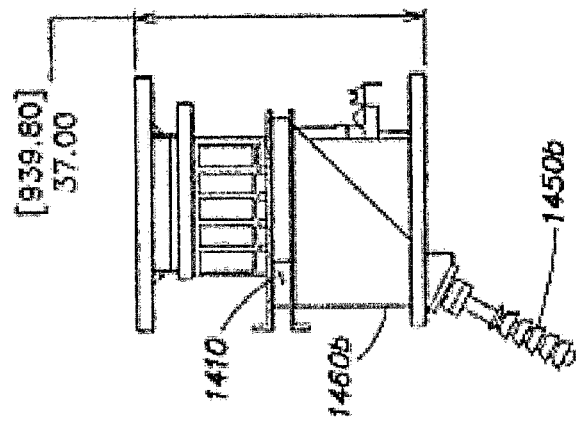
Figure 19C:
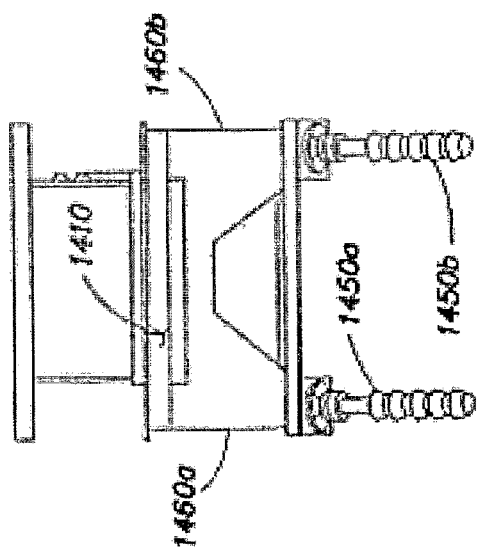
Figure 19B:
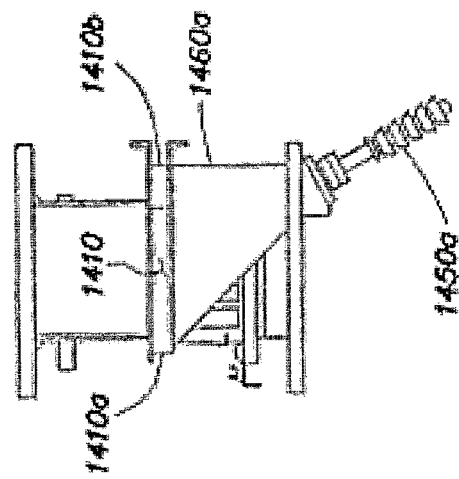
Figure 19E:
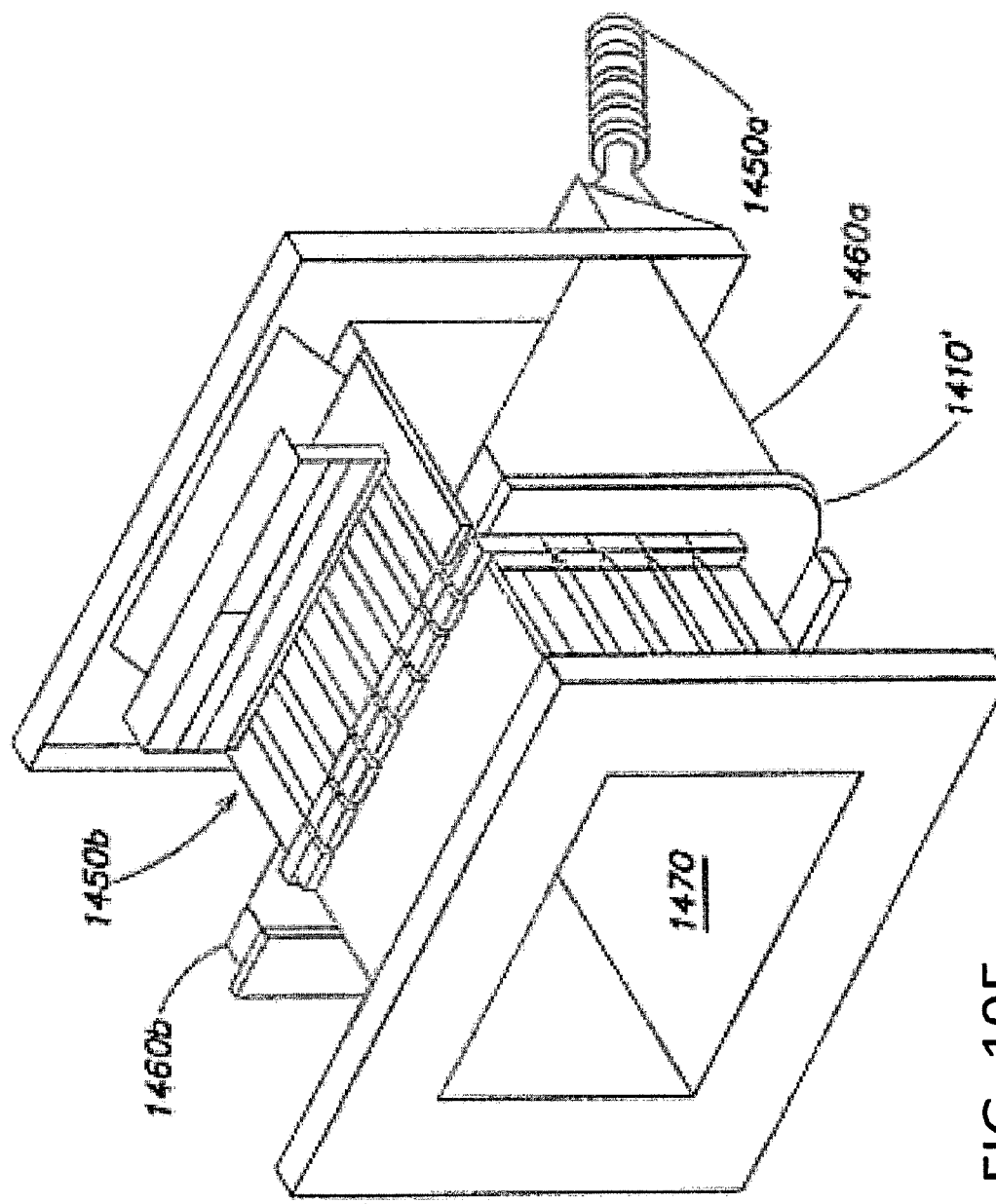
Figure 20:
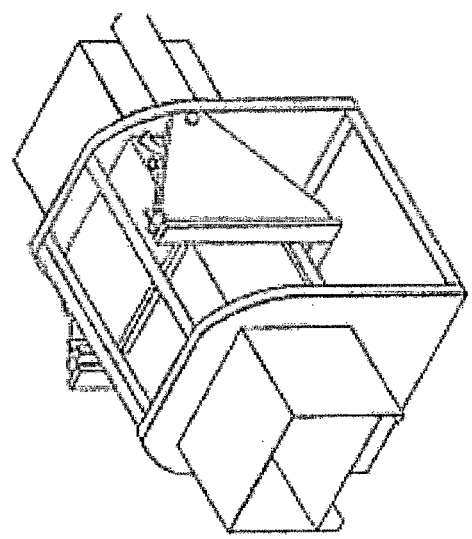
Figure 20:
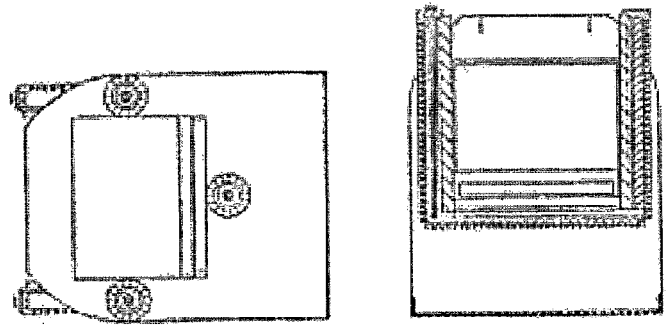
Figure 20:
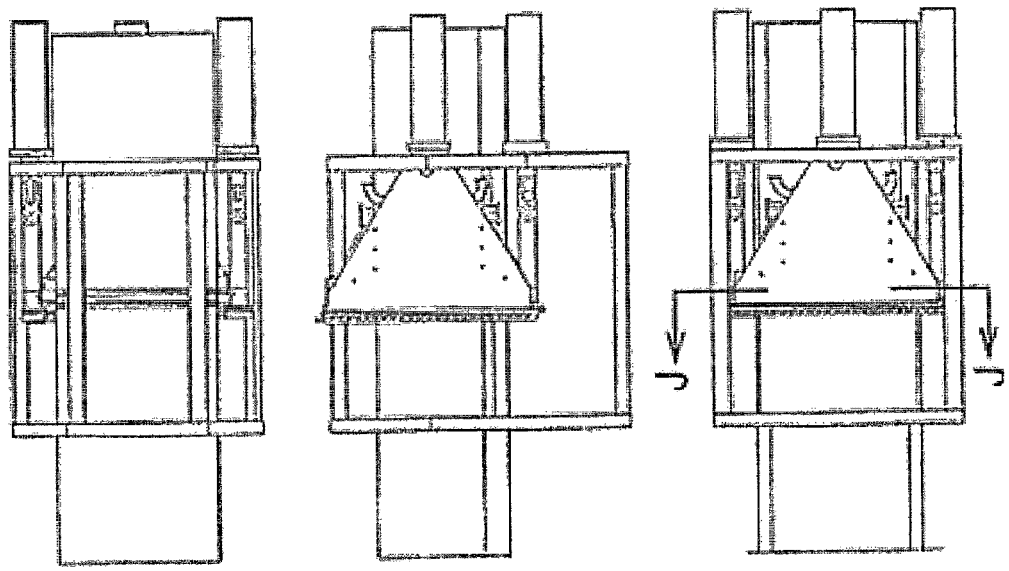
Figure 21:
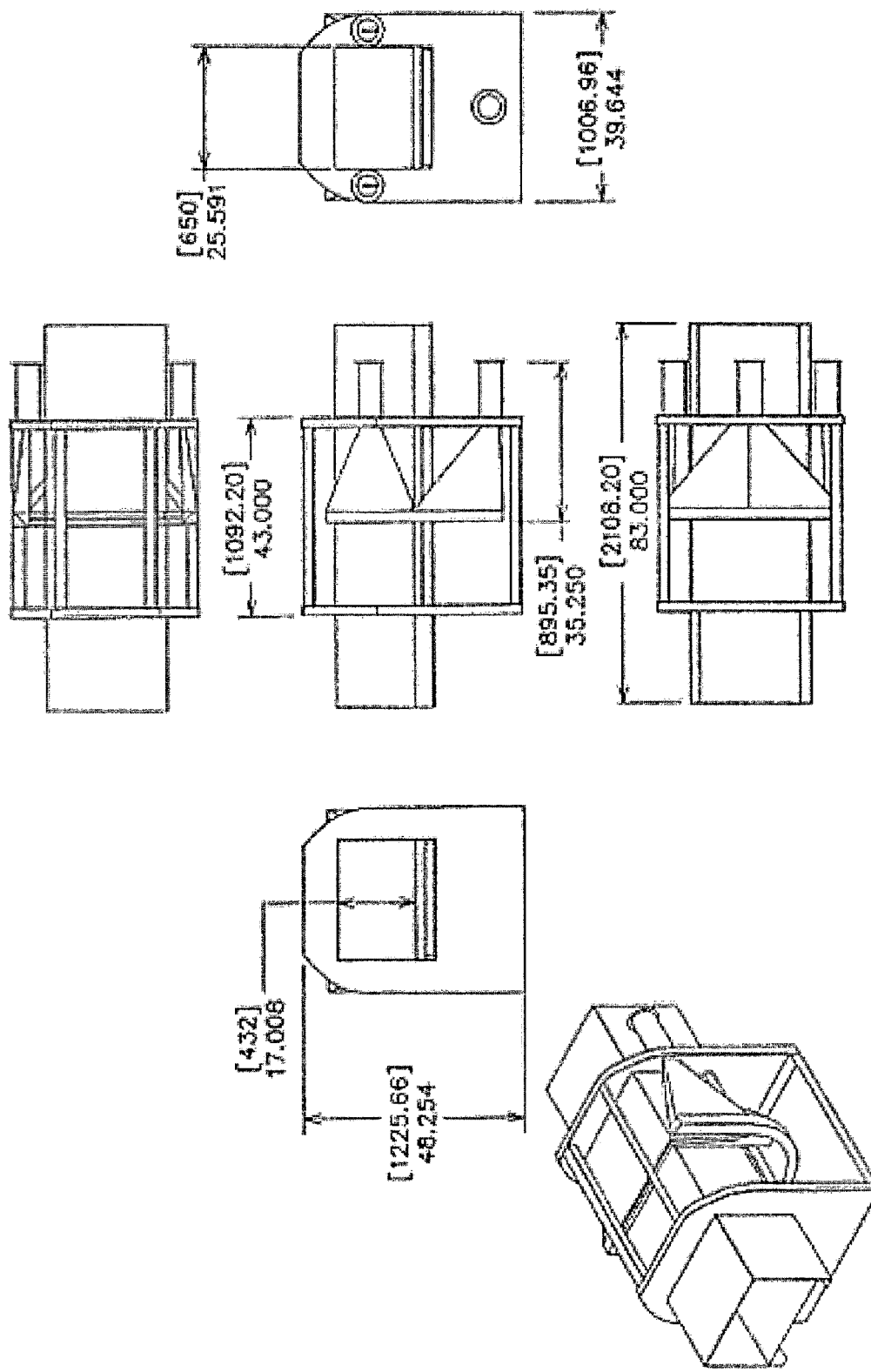

FIG. 12 illustrates portions of an e-beam X-ray scanning system, in accordance with one embodiment of the present invention. X-ray scanning system 2000 includes a non-circular detector array 2200. In particular, detector array 2200 is generally shaped as a rectangular U, sometimes referred to as goal posts, or staple-shaped, comprising substantially linear segments 2210a, 2210b and 2210c. The U-shaped geometry is merely exemplary of an arbitrary geometry array, which as the name suggests, may take on any shape, as the aspects of the invention are not limited in this respect. The various segments of the detector array may be continuous or they may be staggered, for example, along the z-axis, as described in further detail below. In accordance with some embodiments of the invention, detector array 2200 may be a sparse detector array that includes a plurality of non-contiguous detectors 2500 position to receive x-ray radiation. The sparsity of the detectors 2500 in detector array 220 is not a limiting factor of embodiments of the invention, as discussed above in connection with circular sparse detector arrays.

To irradiate the detector array 2200, a target 2010 that generally mimics the shape of detector array 2200 is positioned concentrically and diametrically from the detector array and operates as the e-beam anode. Though, it should be appreciated that a target of any suitable size and position may be used.

The term "diametric" refers herein to positioning of a target and detector array in an opposing arrangement such that diametric portions of the detector array and target are generally facing one another such that x-rays emitted from the portions of the target impinge on the diametrically arranged portions of the detector array. Target 2010 includes substantially linear segments 2012a, 2012b, and 2012c and circular arc segments 2014a and 2014b. Accordingly, linear segment 2210c of the detector array is arranged diametrically to linear segment 2012a because the x-ray sensitive regions of the detectors on segment 2210c are facing target segment 2012a Similarly, segments 2010b and 2010c of the detector array are arranged diametrically to circular segment 2014a of the target. As discussed above, target 2010 may be formed from any material that converts energy from an impinging e-beam into X-rays, such as tungsten, molybdenum, etc. Though, it should be appreciated that a target of any suitable size and position may be used.

To minimize the deflection angle without unduly compromising the size of the inspection area, Applicant has appreciated that multiple e-beam generators, also referred to as electron guns, may be used. In addition, if the required deflection angle may be reduced for a given size target, then, rather than reducing the deflection angle, the same actual deflection angle may be used and the distance between the steering coils and the target may be reduced, as discussed in further detail below. This reduction in distance allows the vacuum tubes through which the e-beams travel after leaving the steering coils to be made smaller, substantially reducing both the cost and bulk of the resulting inspection system.

For example, a first electron gun may be deployed to scan portion $2010a$ of target $2010$ and a second electron gun may be deployed to scan portion $2010b$. In one embodiment, each electron gun scans substantially half of the target, and in a sequential fashion. By positioning the electron gun pair to scan substantially half of the array, the deflection angles for each gun may be reduced. For example, the electron guns may be positioned such that the e-beam would impinge somewhere along the respective target in the absence of deflection forces, rather than passing through, for example, a center point of the inspection region.

Alternatively, the electron beams, in the absence of deflection forces, may pass through points closer to respective portions of the target, rather than passing through the center point, or other points generally equidistant from various points along the target. For example, rather than having a single electron gun positioned such that the generated e-beam, in the absence of deflection forces, passes through a center points $2032$ (as shown in FIG. 12), a pair of electron guns may be positioned such that their e-beams, in the absence of deflection forces, pass through points $2034a$ and $2034b$, respectively. Multiple e-beam generators may be used in numerous configurations to reduce the required deflection angle and/or reduce vacuum tube sizes, as discussed in further detail below.

It should be appreciated that the target 2010 depicted in FIG. 12 is idealized. During operation of an e-beam imaging system (e.g., X-ray scanning system 2000), the target 2010 may undergo thermal expansion. As such, the target 2010 may comprise segments $2012a$, $2014a$, $2012b$, $2010d$, $2010c$, $2014b$, and $2012c$, each of which may expand during operation of the imaging system. Accordingly, the above-mentioned target segments may be arranged so as to accommodate any potential future thermal expansion. For example, the substantially-linear segments $2010c$ and $2010d$ may not be joined and there may be a small gap between these segments to provide space into which these segments may expand during operation. The gap may be of any suitable size to accommodate the expansion of target segments, and may be, for example, a 10 mm gap. Though, a gap of any appropriate size may be used.

Similarly, other segments of the target 2010 may not be contiguously arranged, and may be arranged with gaps among them in order to accommodate for their thermal expansion.

The presence of gaps between target segments may impact the range of angles that each voxel of the imaged target may be imaged from. For instance, the presence of a gap between the two L-shaped sections of the target 2010, as shown by blocks $2010a$ and $2010b$ in FIG. 12, may lead to a number of voxel being irradiated from a smaller range of angles than they would be if the L-shaped sections were joined. In turn, this may violate the geometric constraints required for direct volumetric image reconstruction methods to produce an accurate volumetric image of an imaged object.

Further, gaps between target segments may arise in other ways. For example, though the idealized target of FIG. 12 is shown as generally a unitary structure, in some embodiments, radiation from multiple angles around a tunnel may be provided by multiple sources positioned around the tunnel Multiple sources may be used to simplify the construction of the sources in the aggregate. For example a target and a source of an electron beam may be sealed within an enclosure in which a vacuum is created to better allow the electron beam to propagate. Sealing a target that spans approximately 180 degrees of arc around a tunnel may require an enclosure that is larger than may be required if multiple sources, each spanning only a portion of the way around the tunnel are used. However, using separate enclosures between separate sources may result in further gaps in the angular coverage.

Moreover, other geometric constraints may lead to artifacts or other conditions that limit the accuracy of a volumetric image computed using a direct technique. For example, even in the idealized representation of FIG. 12, there source and detector are not positioned symmetrically around the tunnel, such that there may be portions of the tunnel which are exposed to radiation from a different number of directions than others. Nonetheless, even with systems with these geometric constraints, techniques as described, using a combination of direct reconstruction and iterative processing to reconstruct a final image may be used to accurately reconstruct an image.

Multiple e-beam generators may be arranged to scan the target 2010. In some embodiments, two electron guns are housed in respective and independent vacuum tubes, disposed to scan respective portions of the target in each vacuum tube. Other electron gun/vacuum tube arrangements may be used, as the aspects of the invention are not limited in this respect. FIGS. 13-21 illustrate various arrangements of an X-ray system employing two e-beam generators (guns), in accordance with different embodiments of the present disclosure. In the embodiments illustrates in FIGS. 13-21, the target, in the aggregate, is substantially horseshoe shaped, made up of L-shaped segments in each vacuum tube. In this embodiment, the detector array is substantially u-shaped. However, it should be appreciated that both the target and the detector array may be of substantially the same shape, or of different shapes not illustrated herein, as the aspects of the invention are not limited in this respect.

Inspection systems in accordance with embodiments of the invention may include one or more processors for deriving an image of an item for inspection using, at least in part, an iterative reconstruction process. In some embodiments, the iterative reconstruction process may be initialized with an initial volumetric image estimate as such an initialization may result in fewer overall iterations to obtain an accurate final volumetric image. For example, the computational expense of performing a large number of iterations to compute a high-resolution volumetric image may be a drawback to using iterative reconstruction methods in isolation, because many imaging systems, such as luggage inspection systems deployed in airports, must be able to image objects quickly. The combination of operational time constraints and the computational demands of iterative methods effectively limits the resolution at which an object may be practicably imaged—potentially leading to breaches in security when aspects of an item in the luggage (e.g., explosive) are not accurately reconstructed.

Any suitable method may be used to provide an initial volumetric image estimate to an iterative reconstruction technique. For instance, a direct volumetric reconstruction method such as filtered back projection (FBP) or Fourier reconstruction may be used. Alternatively, direct reconstruction methods such as the analytic cone beam method or the approximate cone beam method may be used. Alternatively, multiple volumetric images using different direct reconstruction methods may be computed first, and the initial volumetric image estimate may be selected among these images based on a suitable error criterion. Additionally, methods other than direct reconstruction methods may be used to provide an initial volumetric estimate, as the embodiments are not limited in this respect.

As should be appreciated from the foregoing, x-ray imaging systems designed according to the principles described herein, may produce an economical, fast and accurate images with fewer detector components and reduced cost.

Alterations, modifications, and improvements are intended to be part of this disclosure, and are intended to be within the spirit and scope of the invention. Accordingly, the foregoing description and drawings are by way of example only.

Although the embodiments described herein relate to an inspection system often employed at a security checkpoint to screen objects such as luggage, other imaging systems that include sparse detector arrays in accordance with embodiments of the invention are also contemplated to reduce the cost of such systems. For example, some embodiments may be directed to an imaging system configured to non-destructively image objects, such as engines. Such systems may include a rotatable table on which the object may be placed within the inspection area for imaging using embodiments of the invention. Other embodiments may be directed to medical applications including an inspection system that includes a patient table or couch on which a patient is placed for insertion into an inspection area of a medical imaging system that employs a sparse detector array. Yet other embodiments are directed to imaging systems configured to image small animals such as mice and rats using, for example, micro-CT or SPECT imaging techniques. Such systems incorporate a sparse detector array and may additionally include a table for placement of an animal for imaging at least a portion of the animal Other imaging system, while not explicitly described, are also contemplated as embodiments of the invention, provided they include a sparse detector array as discussed herein.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface including keyboards, and pointing devices, such as mice, touch pads, and digitizing tables. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. By way of example, and not limitation, computer readable media may comprise computer storage media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

The invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An inspection system, comprising:
    an inspection area;
    at least one x-ray source adapted to emit x-ray radiation into the inspection area;
    a sparse detector array positioned to receive x-ray radiation from the at least one x-ray source after passing through the inspection area, wherein the sparse detector array includes a plurality of rows of detector elements, wherein at least some of the plurality of rows are separated by gaps such that the at least some of the plurality of rows are non-contiguous, wherein a percentage of rows in the sparse detector array compared to a full array of detectors is less than 50%; and
    at least one processor programmed to:
        determine a first volumetric image of at least a portion of an item within the inspection area using a direct reconstruction process from outputs of the sparse detector array when irradiated by the at least one x-ray source;
        initialize an iterative reconstruction process with the first volumetric image; and
        perform the iterative reconstruction process to determine a second volumetric image of at least a portion of the item within the inspection area.

2. The inspection system of claim 1, further comprising a rotatable gantry, wherein the at least one x-ray source and the sparse detector array are mounted on opposite sides of the rotatable gantry.

3. The inspection system of claim 1, further comprising a conveyor arranged between the at least one x-ray source and the sparse detector array, wherein the conveyor is configured to transport the item through the inspection area.

4. The inspection system of claim 1, wherein a size of the gaps between the rows of the sparse detector array varies along a length of the sparse detector array.

5. The inspection system of claim 4, wherein at least some gaps between rows in the center of the sparse detector array are smaller than gaps between rows at the edges of the sparse detector array.

6. The inspection system of claim 5, wherein at least some rows in the center of the sparse detector array are arranged without gaps between the rows such that the at least some rows in the center of the sparse detector array are contiguous.

7. The inspection system of claim 1, wherein the inspection system is a computed tomography system.

8. The inspection system of claim 2, wherein the plurality of rows of detector elements of the sparse detector array are arranged in an arc on the rotating gantry, and wherein the sparse detector array further comprises at least one additional row of detector elements arranged inside of the arc including the plurality of rows of detector elements.

9. The inspection system of claim 8, wherein the at least one additional row of detector elements comprises at least two additional rows of detector elements arranged on either end of the sparse detector array.

10. The inspection system of claim 1, wherein the percentage of rows in the sparse detector array compared to a full array of detectors is less than 25%.

11. The inspection system of claim 1, wherein the plurality of rows in the sparse detector array are arranged at an angle relative to a moving direction of a conveyor passing through the inspection area.

12. The inspection system of claim 1, further comprising a conveyor passing through the inspection area, wherein a first distance between the conveyor and the at least one x-ray source is greater than a second distance between the conveyor and the sparse detector array.

13. The inspection system of claim 1, wherein the at least one x-ray source comprises a stationary x-ray source with a plurality of sequential time-multiplexed source positions, and wherein the sparse detector array comprises a fixed detector array arranged to receive x-ray radiation emitted from the stationary x-ray source at each of the plurality of sequential time-multiplexed source positions.

14. The inspection system of claim 13, wherein the stationary x-ray source is an e-beam.

15. The inspection system of claim 1, wherein the at least one x-ray source is configured to emit x-ray radiation having multiple energies including a first energy and a second energy, and wherein the sparse detector array comprises:
    a first subset of detector elements more sensitive to x-ray radiation having the first energy than x-ray radiation having the second energy; and
    a second subset of detector elements more sensitive to x-ray radiation having the second energy than x-ray radiation having the first energy.

16. The inspection system of claim 1, wherein the at least one x-ray source is configured to emit x-ray radiation having multiple energies including a first energy and a second energy, and wherein at least some of the detector elements in the sparse detector array are configured to classify x-ray radiation received from the at least one x-ray source as having the first energy or the second energy.

17. The inspection system of claim 16, wherein the at least some of the detector elements in the sparse detector array configured to classify x-ray radiation are configured to record individual x-ray photons as having the first energy or the second energy.

18. The inspection system of claim 1, wherein the at least one x-ray source comprises a carbon nanotube x-ray source including a plurality of switchable carbon nanotubes that, when activated in time-sequence by a voltage, emit x-ray radiation.

19. The inspection system of claim 1, wherein the at least one x-ray source comprises a distributed array of switchable x-ray sources that, when activated in time-sequence, emit x-ray radiation.

20. The inspection system of claim 1, wherein the at least one x-ray source comprises a multi-energy x-ray source configured to emit first x-ray radiation having a first energy when a first voltage is applied to the multi-energy x-ray source and configured to emit second x-ray radiation having a second energy when a second voltage is applied to the multi-energy x-ray source.

21. The inspection system of claim 1, wherein at least some of the plurality of rows in the sparse detector array are arranged in layers for multi-energy discrimination of the x-ray radiation received from the at least one x-ray source.

22. The inspection system of claim 2, further comprising:
a power supply adapted to provide power to the at least one x-ray source, wherein the power supply is configured to conform to the structure of the rotating gantry.

23. The inspection system of claim 1, further comprising a rotatable gantry, wherein the at least one x-ray source is mounted on the rotatable gantry and wherein the sparse detector array is stationary.

24. The inspection system of claim 1, further comprising a rotatable platform configured to rotate an object to be imaged within the inspection area.

25. The inspection system of claim 1, further comprising a movable table configured to facilitate the placement of a patient within the inspection area for generating a volumetric image of at least a portion of the patient.

26. The inspection system of claim 1, wherein the inspection system is adapted for imaging small animals and wherein the inspection system further comprises a table configured to facilitate the placement of an animal within the inspection area for generating a volumetric image of at least a portion of the animal.

27. A computer-implemented method for deriving an output volumetric image of an object in an inspection area of an x-ray system, wherein the x-ray system includes a sparse detector array having a plurality of non-contiguous rows of detector elements, wherein a percentage of rows in the sparse detector array compared to a full array of detectors is less than 50%, the method comprising:
receiving at the detector elements in the sparse detector array, a plurality of radiation measurements indicating amounts of radiation passing through the object from different directions, wherein the plurality of radiation measurements include sparsely-spaced measurements in a fan-beam direction of radiation passing through the object;
determining a first volumetric image of the object using a direct reconstruction process from the plurality of radiation measurements;
initializing an iterative reconstruction process with the first volumetric image of the object; and
performing at least one iteration of the iterative reconstruction process from the plurality of radiation measurements to derive the output volumetric image of the object.

28. The computer-implemented method of claim 27, wherein the iterative reconstruction process comprises ordered-subset maximum likelihood, algebraic reconstruction technique, simultaneous algebraic reconstruction technique, simultaneous iterative reconstruction technique, least squares QR method, expectation maximization, ordered-subset expectation maximization, convex method, or orders subset convex method.

29. The computer-implemented method of claim 27, wherein the direct reconstruction process comprises filtered back projection, direct Fourier reconstruction, analytic cone beam method, or approximate cone beam method.

30. An inspection system, comprising:
at least one x-ray source positioned to emit x-ray radiation toward an inspection area in a tunnel, wherein the tunnel includes a conveyor configured to enable an object placed thereon to pass through the inspection area;
a sparse detector array positioned to receive the x-ray radiation passing through the object, wherein the sparse detector array includes a plurality of rows of detector elements, wherein the detector elements in each row are oriented along the moving direction of the conveyor, and wherein the sparse detector array includes gaps between at least some of the plurality of rows in a direction perpendicular to the moving direction of the conveyor, wherein a percentage of rows in the sparse detector array compared to a full array of detectors is less than 50%; and
at least one processor programmed to
determine a first volumetric image of at least a portion of the object using a direct reconstruction process from outputs of the sparse detector array when irradiated by the at least one x-ray source;
initialize an iterative reconstruction process with the first volumetric image; and
perform the iterative reconstruction process to determine a second volumetric image of at least a portion of the object.

31. The inspection system of claim 30, wherein the detector elements in at least one row of the sparse detector array are angled with respect to the moving direction of the conveyor.

* * * * *